United States Patent
Kamatani et al.

(10) Patent No.: US 9,240,554 B2
(45) Date of Patent: Jan. 19, 2016

(54) ORGANIC COMPOUND, ORGANIC ELECTROLUMINESCENCE ELEMENT, AND IMAGE DISPLAY DEVICE

(75) Inventors: Jun Kamatani, Tokyo (JP); Naoki Yamada, Inagi (JP); Masashi Hashimoto, Tokyo (JP); Takayuki Horiuchi, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 187 days.

(21) Appl. No.: 13/980,528

(22) PCT Filed: Dec. 9, 2011

(86) PCT No.: PCT/JP2011/079119
§ 371 (c)(1),
(2), (4) Date: Jul. 18, 2013

(87) PCT Pub. No.: WO2012/098793
PCT Pub. Date: Jul. 26, 2012

(65) Prior Publication Data
US 2013/0300638 A1    Nov. 14, 2013

(30) Foreign Application Priority Data

Jan. 20, 2011   (JP) ................................ 2011-009529

(51) Int. Cl.
| | |
|---|---|
| H01L 51/00 | (2006.01) |
| C09K 11/06 | (2006.01) |
| H01L 51/50 | (2006.01) |
| H05B 33/14 | (2006.01) |
| C07C 255/52 | (2006.01) |
| C07C 211/61 | (2006.01) |
| C07C 13/62 | (2006.01) |
| C07F 7/08 | (2006.01) |
| C07D 213/06 | (2006.01) |
| C07C 25/22 | (2006.01) |
| H01L 27/32 | (2006.01) |

(52) U.S. Cl.
CPC ............ *H01L 51/0056* (2013.01); *C07C 13/62* (2013.01); *C07C 25/22* (2013.01); *C07C 211/61* (2013.01); *C07C 255/52* (2013.01); *C07D 213/06* (2013.01); *C07F 7/0809* (2013.01); *C09K 11/06* (2013.01); *H01L 27/3244* (2013.01); *H01L 51/006* (2013.01); *H01L 51/0067* (2013.01); *H01L 51/0094* (2013.01); *H01L 51/5012* (2013.01); *H05B 33/14* (2013.01); *C07C 2101/14* (2013.01); *C07C 2103/40* (2013.01); *C07C 2103/54* (2013.01); *C09K 2211/1011* (2013.01); *H01L 51/5028* (2013.01)

(58) Field of Classification Search
CPC ...... C07C 13/62; C07C 211/61; C07C 25/22; C07C 255/52; C07C 2101/14; C07C 2103/40; C07C 2103/54; C07D 213/06; C07F 7/0809; C09K 11/06; C09K 2211/1011
See application file for complete search history.

(56) References Cited

U.S. PATENT DOCUMENTS

2010/0270914 A1    10/2010   Kamatani

FOREIGN PATENT DOCUMENTS

| CN | 1327468 A | 12/2001 |
|---|---|---|
| JP | 10-330295 A | 12/1998 |
| JP | 2002-25776 A | 1/2002 |
| JP | 2010-254610 A | 11/2010 |
| JP | 2010-270103 A | 12/2010 |
| JP | 2011-207829 A | 10/2011 |
| JP | 2011-231086 A | 11/2011 |
| WO | 2010123153 A1 | 10/2010 |

*Primary Examiner* — Paul A Zucker
*Assistant Examiner* — Mark Luderer
(74) *Attorney, Agent, or Firm* — Canon U.S.A. Inc., IP Division

(57) ABSTRACT

The present invention provides an organic electroluminescence element having a high luminous efficiency.
An organic electroluminescence element includes an anode, a cathode, and at least one organic compound layer disposed between the anode and the cathode, wherein at least one of the at least one the organic compound layer contains an organic compound shown in Claim 1.

12 Claims, 1 Drawing Sheet

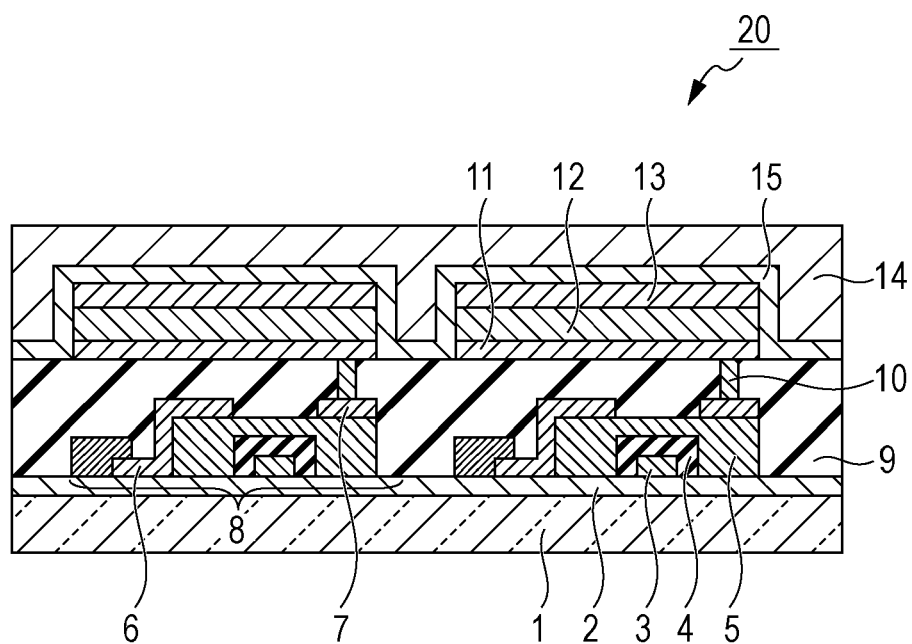

ORGANIC COMPOUND, ORGANIC ELECTROLUMINESCENCE ELEMENT, AND IMAGE DISPLAY DEVICE

TECHNICAL FIELD

The present invention relates to an organic compound, and an organic electroluminescence element and an image display device using the organic compound.

BACKGROUND ART

Organic electroluminescence elements (organic EL elements) are electronic elements each including a pair of electrodes and an organic compound layer disposed between the electrodes. Electrons and holes are injected from the pair of electrodes to generate excitons of a light-emitting organic compound in the organic compound layer, so that the organic electroluminescence elements emit light when the excitons are returned to the ground state.

Organic electroluminescence elements have been recently significantly developed, and characteristics thereof include low drive voltages, a variety of emission wavelengths, high-speed response, and the possibility of reduction in thickness and weight of light-emitting devices.

In addition, light-emitting organic compounds have been actively created so far. This is because the creation of compounds having excellent light emission properties is important for providing high-performance organic electroluminescence elements.

Examples of compounds that have been created so far include compound 1-A described below and proposed in PTL 1.

[Chem. 1]

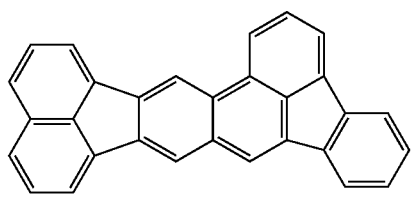

1-A

The compound 1-A has acenaphtho[1,2-k]benzo[e]acephenanthrylene as a basic skeleton. Light emitted from the acenaphtho[1,2-k]benzo[e]acephenanthrylene skeleton is blue light.

PTL 2 proposes compound 1-B below, and PTL 3 proposes compound 1-C below.

[Chem. 2]

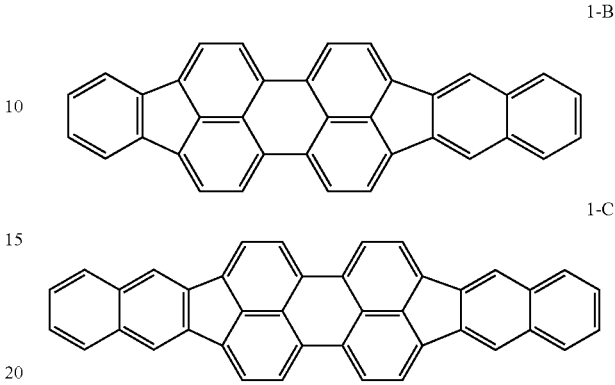

CITATION LIST

Patent Literature

PTL 1 Japanese Patent Laid-Open No. 2010-254610 (US2010/0270914)
PTL 2 Japanese Patent Laid-Open No. 2002-025776
PTL 3 Japanese Patent Laid-Open No. 10-330295

However, the compound 1-B has weak emission intensity, and the compound 1-C has high emission intensity but has large intermolecular interaction because of its high planarity and symmetry. Therefore, the compound 1-C is poor in sublimation.

In addition, the basic skeletons possessed by the compounds described in PTLs 1 to 3 cannot produce compounds having an emission within the red region, a high luminous efficiency, and good sublimability.

SUMMARY OF INVENTION

The present invention provides an organic compound having an emission within the red region and good sublimability. Also, the present invention provides an organic electroluminescence element having a high luminous efficiency.

An organic compound according to the present invention is an organic compound represented by the following general formula (1).

[Chem. 3]

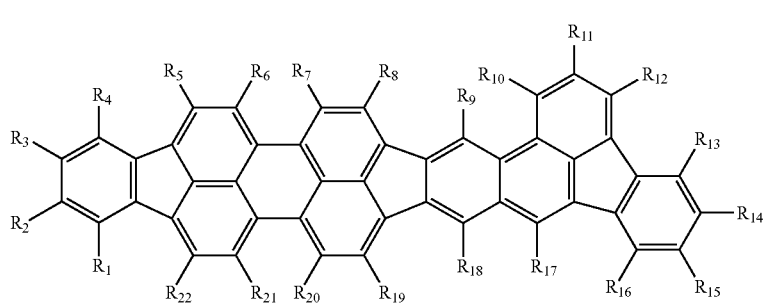

(1)

In the formula (1), $R_1$ to $R_{22}$ are each independently a hydrogen atom or a substituent selected from a halogen atom, a substituted or unsubstituted alkyl group, a substituted or unsubstituted alkoxy group, a substituted or unsubstituted amino group, a substituted or unsubstituted aryl group, a substituted or unsubstituted heterocyclic group, a substituted or unsubstituted aryloxy group, a silyl group, and a cyano group.

The organic compound according to the present invention has a basic skeleton which can emit light within the red region. Therefore, it is possible to provide an organic compound having an emission within the red region and good sublimability.

Also, the organic compound according to the present invention has the characteristic that the basic skeleton has a narrow band gap and deep LUMO. Therefore, it is possible to provide an organic electroluminescence element having a high luminous efficiency.

BRIEF DESCRIPTION OF DRAWINGS

FIG. 1 is a schematic sectional view showing an example of a display device including an organic electroluminescence element according to an embodiment of the present invention and a TFT element as an example of a switching element electrically connected to the organic electroluminescence element.

DESCRIPTION OF EMBODIMENTS

An organic compound according to the present invention is an organic compound represented by the following general formula (1).

[Chem. 4]

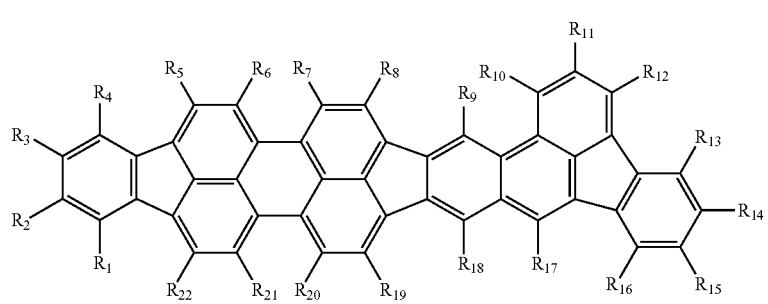

(1)

In the formula (1), $R_1$ to $R_{22}$ are each independently a hydrogen atom or a substituent selected from a halogen atom, a substituted or unsubstituted alkyl group, a substituted or unsubstituted alkoxy group, a substituted or unsubstituted amino group, a substituted or unsubstituted aryl group, a substituted or unsubstituted heterocyclic group, a substituted or unsubstituted aryloxy group, a silyl group, and a cyano group.

In the formula (1), preferably, $R_1$ to $R_{22}$ are each independently a hydrogen atom or a substituent selected from a substituted or unsubstituted alkyl group and a substituted or unsubstituted aryl group.

Examples of a halogen atom represented by $R_1$ to $R_{22}$ include, but of course not limited to, fluorine, chlorine, bromine, iodine, and the like.

Examples of an alkyl group represented by $R_1$ to $R_{22}$ include, but of course not limited to, a methyl group, an ethyl group, a normal propyl group, an isopropyl group, a normal butyl group, a tertiary butyl group, a secondary butyl group, an octyl group, a cyclohexyl group, a 1-adamantyl group, 2-adamantyl group, and the like.

Examples of an alkoxy group represented by $R_1$ to $R_{22}$ include, but of course not limited to, a methoxy group, an ethoxy group, a propoxy group, a 2-ethyl-octyloxy group, a benzyloxy group, and the like.

Examples of an amino group represented by $R_1$ to $R_{22}$ include, but of course not limited to, a N-methylamino group, a N-ethylamino group, a N,N-dimethylamino group, a N,N-diethylamino group, a N-methyl-N-ethylamino group, a N-benzylamino group, a N-methyl-N-benzylamino group, a N,N-dibenzylamino group, an anilino group, a N,N-diphenylamino group, a N,N-dinaphthylamino group, a N,N-difluorenylamino group, a N-phenyl-N-tolylamino group, a N,N-ditolylamino group, a N-methyl-N-phenylamino group, a N,N-dianisolylamino group, a N-mesityl-N-phenylamino group, a N,N-dimesitylamino group, a N-phenyl-N-(4-tertiary butylphenyl)amino group, a N-phenyl-N-(4-trifluoromethylphenyl)amino group, a N-piperidyl group, and the like.

Examples of an aryl group represented by $R_1$ to $R_{22}$ include, but of course not limited to, a phenyl group, a naphthyl group, an indenyl group, a biphenyl group, a terphenyl group, a fluorenyl group, and the like.

Examples of a heterocyclic group represented by $R_1$ to $R_{22}$ include, but of course not limited to, a pyridyl group, an oxazolyl group, an oxadiazolyl group, a thiazolyl group, a thiadiazolyl group, a carbazolyl group, an acridinyl group, a phenanthrolyl group, and the like.

Examples of an aryloxy group represented by $R_1$ to $R_{22}$ include, but of course not limited to, a phenoxy group, a 4-tert-butylphenoxy group, a thienyloxy group, and the like.

Examples of a silyl group represented by $R_1$ to $R_{22}$ include, but of course not limited to, a triphenylsilyl group and the like.

Examples of a substituent which may be further contained in each of the alkyl group, the alkoxy group, the amino group, the aryl group, the heterocyclic group, and the aryloxy group include, but of course not limited to, alkyl groups such as a methyl group, an ethyl group, a normal propyl group, an isopropyl group, a normal butyl group, a tert-butyl group, and the like; aralkyl groups such as a benzyl group and the like; aryl groups such as a phenyl group, a biphenyl group, and the like; heterocyclic groups such as a pyridyl group, a pyrrolyl group, and the like; amino groups such as a dimethylamino group, a diethylamino group, a dibenzylamino group, a diphenylamino group, a ditolylamino group, and the like; alkoxy groups such as a methoxy group, an ethoxy group, a propoxy group, and the like; aryloxy groups such as a phenoxy group and the like; halogen atoms such as fluorine, chlorine, bromine, iodine, and the like; and a cyano group.

In the present invention, $R_1$, $R_2$, $R_3$, $R_4$, $R_9$, and $R_{18}$ in the formula (1) are each a hydrogen atom or a substituted or unsubstituted aryl group. In addition, a compound with suppressed concentration quenching can be produced by introducing a substituent into the basic skeleton of the organic compound according to the present invention. Further, from the viewpoint of suppression of concentration quenching, $R_9$ and $R_{18}$ in the formula (1) are each a phenyl group.

Next, a method for synthesizing the organic compound according to the present invention is described. The organic compound according to the present invention is synthesized, for example, according to a reaction scheme shown below.

As shown in the above-described synthesis scheme, the organic compound according to the present invention is synthesized using the following compounds (a) to (d) as raw materials.

(a) Diketone derivative (D0)
(b) Acetone derivative (D1)
(c) Fluoranthenyl amine derivative (D2)
(d) Fluoranthenyl boronic acid ester derivative (D3)

In this case, a hydrogen atom of any one of $R_1$ to $R_{22}$ in the formula (1) is substituted by a predetermined substituent by introducing a proper substituent into any one of the compounds (a) to (d). Examples of the substituent introduced include an alkyl group, a halogen atom, a phenyl group, and the like.

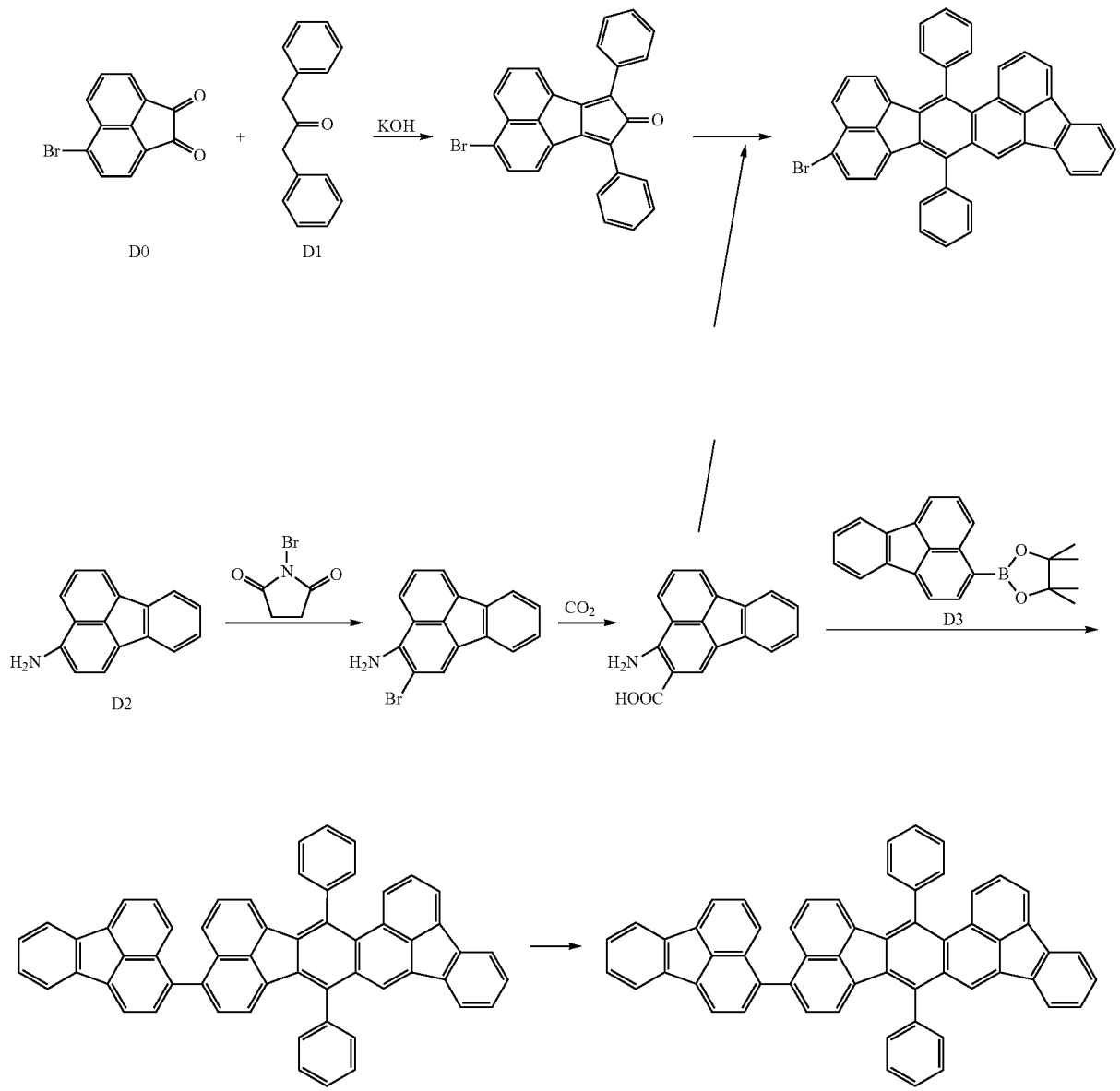

[Chem. 5]

In the synthesis scheme, various organic compounds can be synthesized by changing D1 to D3. Examples of the organic compounds, together with the raw materials D1 to D3, are shown in Table 1 below.

TABLE 1

| Synthesis example | D1 | D2 | D3 |
|---|---|---|---|
| 1 | | | |
| 2 | | | |
| 3 | | | |
| 4 | | | |
| 5 | | | |
| 6 | | | |

TABLE 1-continued
| 7 | 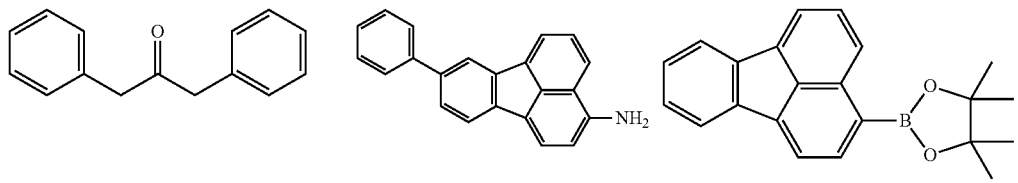 | | |
| 8 | 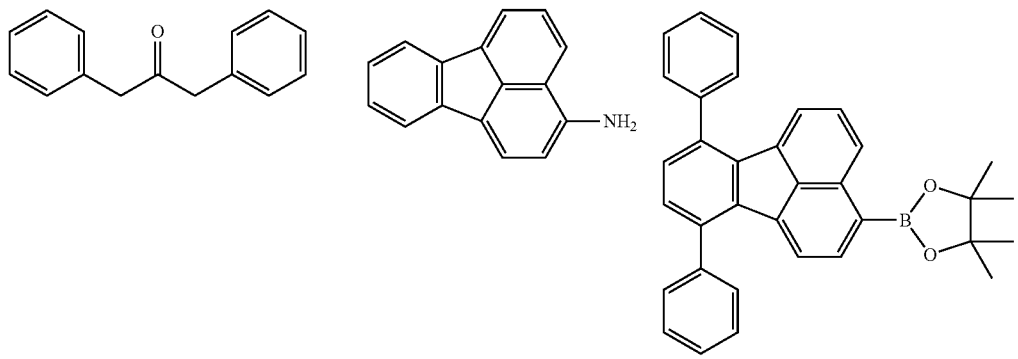 | | |
| 9 | 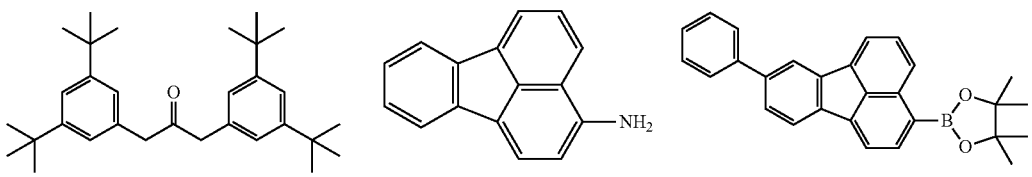 | | |
| Synthesis Example | Synthetic compound | Exemplified compound |
|---|---|---|
| 1 | 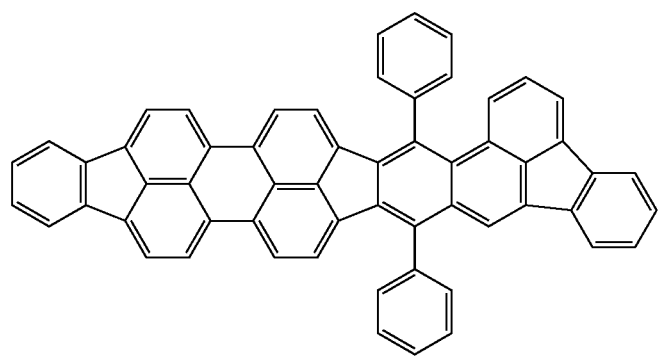 [SMILES: c1ccc(-c2c3cc4c5ccccc5c5cccc(c3c(-c3ccccc3)c3c6ccc7c8ccc9c%10c(ccc(c%11ccc(c23)c6c%117)c%108)-c2ccccc2-9)c54)cc1] | A2 |
| 2 | 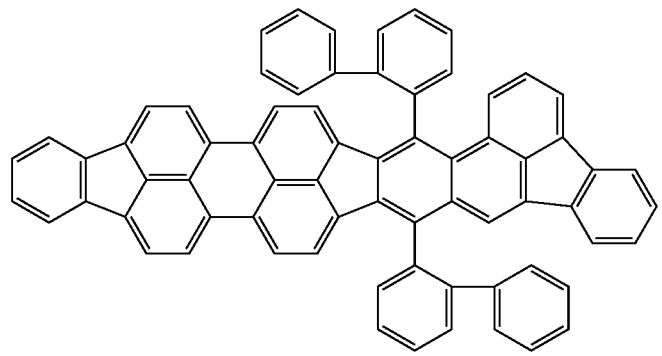 [SMILES: c1ccc(-c2ccccc2-c2c3cc4c5ccccc5c5cccc(c3c(-c3ccccc3-c3ccccc3)c3c6ccc7c8ccc9c%10c(ccc(c%11ccc(c23)c6c%117)c%108)-c2ccccc2-9)c54)cc1] | A3 |

TABLE 1-continued
| | | |
|---|---|---|
| 3 | 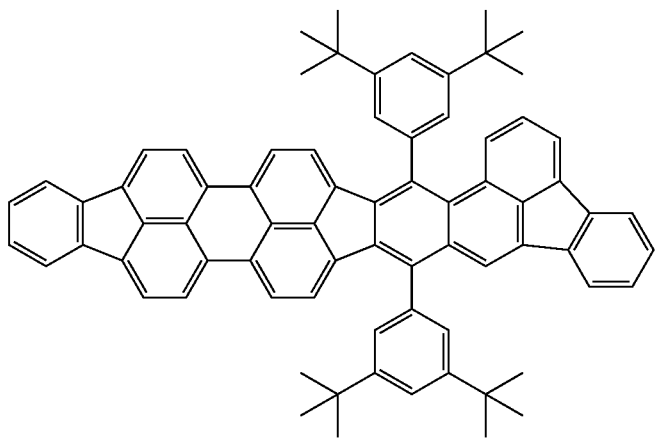 [SMILES: CC(C)(C)c1cc(-c2c3cc4c5ccccc5c5cccc(c3c(-c3cc(C(C)(C)C)cc(C(C)(C)C)c3)c3c6ccc7c8ccc9c%10c(ccc(c%11ccc(c23)c6c%117)c%108)-c2ccccc2-9)c54)cc(C(C)(C)C)c1] | A6 |
| 4 | 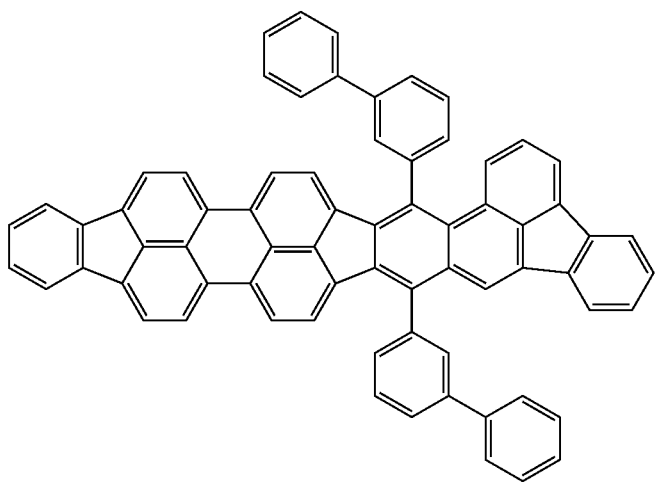 [SMILES: c1ccc(-c2cccc(-c3c4cc5c6ccccc6c6cccc(c4c(-c4cccc(-c7ccccc7)c4)c4c7ccc8c9ccc%10c%11c(ccc(c%12ccc(c34)c7c%128)c%119)-c3ccccc3-%10)c65)c2)cc1] | A7 |
| 5 | 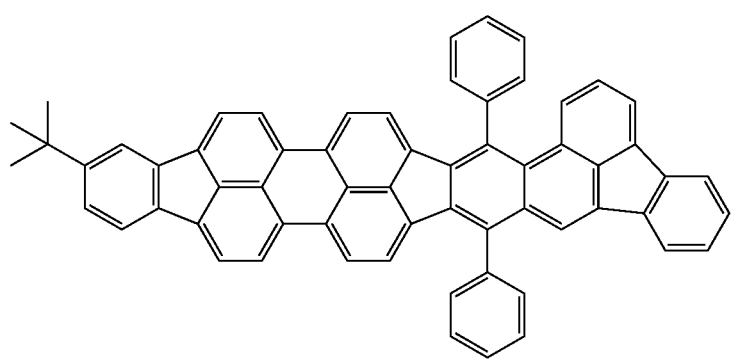 [SMILES: CC(C)(C)c1ccc2c(c1)-c1ccc3c4ccc5c6c(-c7ccccc7)c7c(cc8c9ccccc9c9cccc7c98)c(-c7ccccc7)c6c6ccc(c7ccc-2c1c73)c4c65] | A11 |
| 6 | 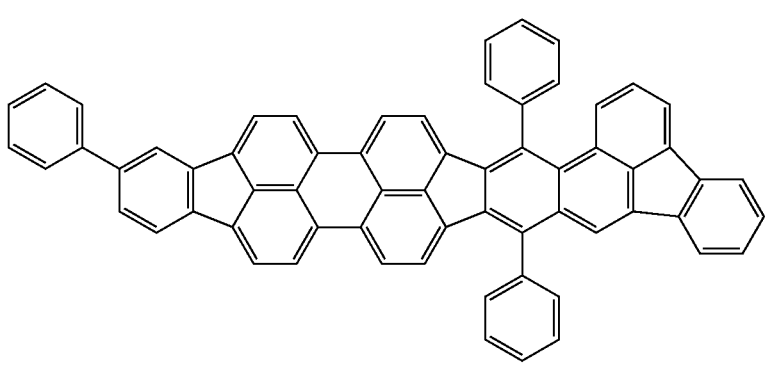 [SMILES: c1ccc(-c2ccc3c(c2)-c2ccc4c5ccc6c7c(-c8ccccc8)c8c(cc9c%10ccccc%10c%10cccc8c%109)c(-c8ccccc8)c7c7ccc(c8ccc-3c2c84)c5c76)cc1] | A14 |

TABLE 1-continued

| | | |
|---|---|---|
| 7 | 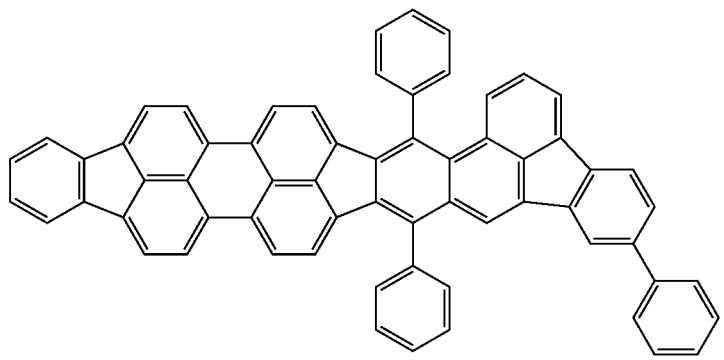 [SMILES: c1ccc(-c2ccc3c(c2)c2cc4c(-c5ccccc5)c5c6ccc7c8ccc9c%10c(ccc(c%11ccc(c5c(-c5ccccc5)c4c4cccc3c24)c6c7%11)c%108)-c2ccccc2-9)cc1] | A16 |
| 8 | 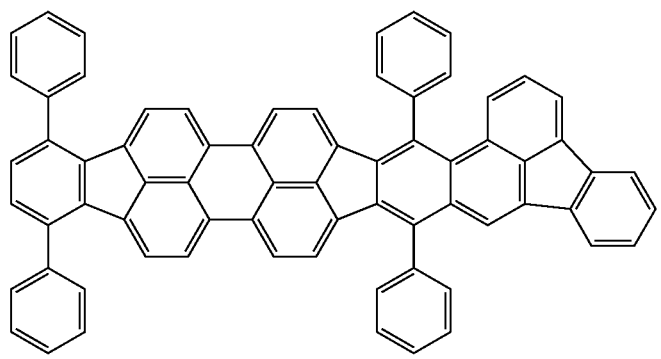 [SMILES: c1ccc(-c2ccc(-c3ccccc3)c3c2-c2ccc4c5ccc6c7c(-c8ccccc8)c8cc9c%10ccccc%10c%10cccc(c8c(-c8ccccc8)c7c7ccc(c8ccc-3c2c48)c5c67)c%109)cc1] | A17 |
| 9 | 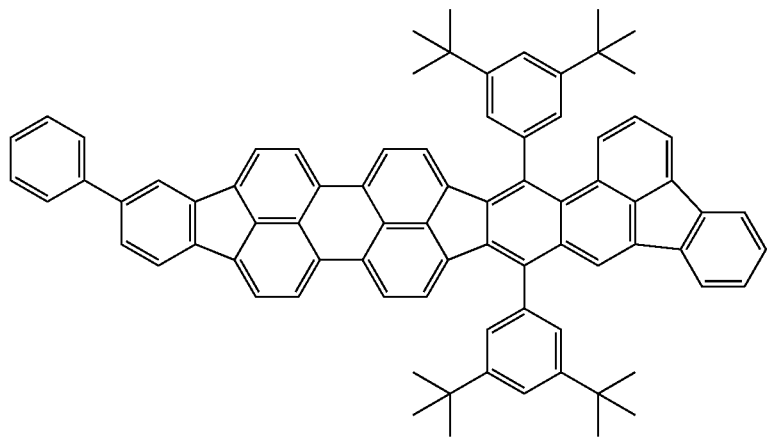 [SMILES: CC(C)(C)c1cc(-c2c3cc4c5ccccc5c5cccc(c3c(-c3cc(C(C)(C)C)cc(C(C)(C)C)c3)c3c6ccc7c8ccc9c%10c(ccc(c%11ccc(c23)c6c%117)c%108)-c2ccc(-c3ccccc3)cc2-9)c54)cc(C(C)(C)C)c1] | A24 |

Next, the characteristics of the organic compound according to the present invention are described.

In order to develop the organic compound represented by the formula (1), the inventors paid attention to the basic skeleton thereof. Specifically, the inventors attempted to provide an organic compound in which only the basic skeleton molecule has an emission wavelength within a desired emission wavelength region.

A known method for achieving a desired emission wavelength includes controlling the emission wavelength of a compound by providing a specified substituent to its basic skeleton. However, this method may impair the stability of the compound.

In the present invention, the desired emission wavelength region to be provided in the compound is the red region, and specifically 580 nm or more and 650 nm or less.

Next, the characteristics of the organic compound according to the present invention are described by comparison with comparative compounds having structures similar to the organic compound of the present invention. Specifically, description is made by comparison with compounds represented by the following formulae (2), (3), and (4).

[Chem. 6]

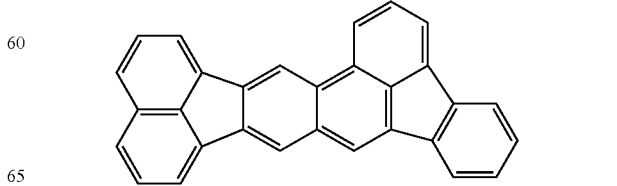

(2)

(3)

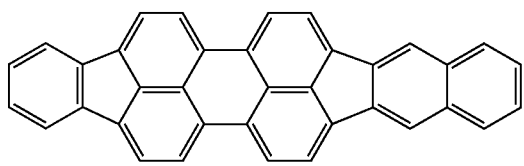

(4)

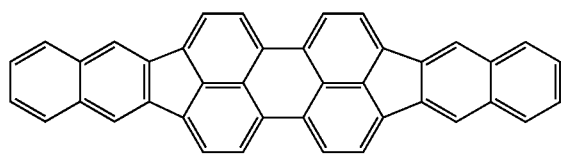

The organic compound according to the present invention is a compound having a basic skeleton represented by the following formula (5).

[Chem. 7]

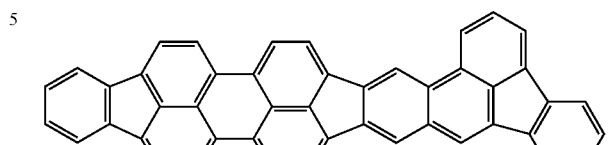

(5)

Here, the inventors made a comparison of light emission properties and sublimability between an organic compound represented by the formula (5) which is substituted by phenyl groups and organic compounds represented by the formulae (2), (3), and (4) each of which is substituted by phenyl groups. The results are shown in Table 2 below. Among the evaluation items shown in Table 2, the sublimability was evaluated by heating a sample under the condition of a degree of vacuum of about $5.0\times10^{-4}$ Pa.

TABLE 2

| Compound | Structural formula | Peak emission wavelength [nm] | Quantum yield | Bublimability |
|---|---|---|---|---|
| a |  | 440 | 0.79 | ○ |
| b |  | 580 | 0.48 | ○ |

TABLE 2-continued

| Compound | Structural formula | Peak emission wavelength [nm] | Quantum yield | Bublimability |
|---|---|---|---|---|
| c | 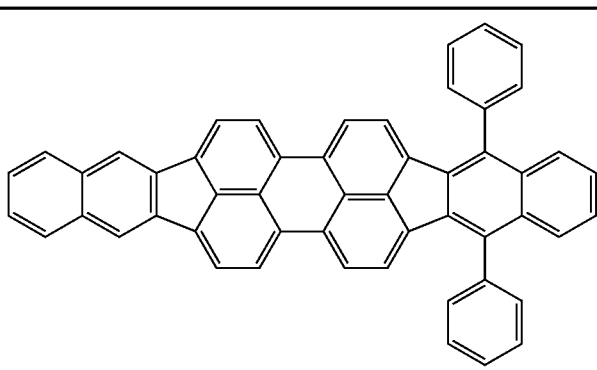 | 597 | 0.60 | With decomposition |
| d | 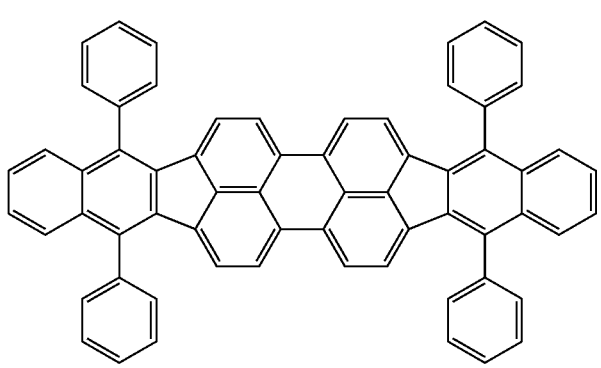 [SMILES: c1ccc(-c2c3c(c(-c4ccccc4)c4ccccc24)-c2ccc4c5ccc6c7c(ccc(c8ccc-3c2c84)c75)-c2c-6c(-c3ccccc3)c3ccccc3c2-c2ccccc2)cc1] | 597 | 0.62 | With decomposition |
| e | 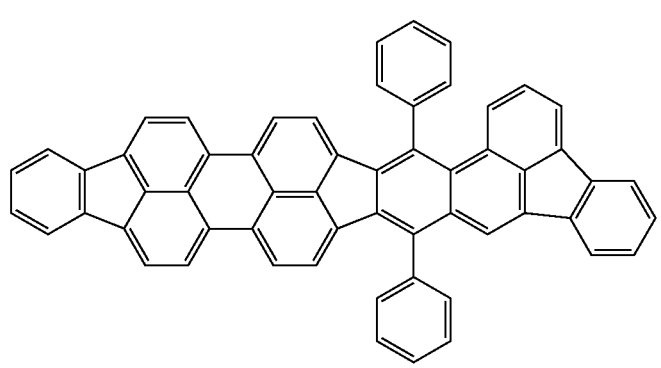 [SMILES: c1ccc(-c2c3cc4c5ccccc5c5cccc(c3c(-c3ccccc3)c3c6ccc7c8ccc9c%10c(ccc(c%11ccc(c23)c6c%117)c%108)-c2ccccc2-9)c54)cc1] | 582 | 0.60 | ○ |

Table 2 indicates that the luminescent color of the compound a is blue. However, the emission of the compound is significantly different from the light emission characteristic (red light emission) required in the present invention. Therefore, the compound a is unsuitable as a red light-emitting material required in the present invention.

Table 2 indicates that the luminescent color of the compound b is red, but the quantum yield is 0.48 which is clearly lower than those of the other compounds (compound a, compound c, compound d, and compound e). This represents that in use as a light-emitting material, the energy generated by recombination of holes and electrons cannot be efficiently converted to light. Therefore, the compound b is unsuitable as a light-emitting material.

It is also found from Table 2 that the compounds c and d exhibit a red luminescent color and high quantum yield, but sublimation is accompanied by decomposition.

On the other hand, Table 2 indicates that the compound e which is an organic compound according to the present invention has a red light emission because of its emission wavelength of 582 nm and has a high emission quantum yield. In addition, the compound e exhibits good sublimability without being associated with decomposition during sublimation.

Now, the reason for differences in sublimability between the compounds c and d and the compound e is described below.

The compounds c and d shown in Table 2 are compounds each having an organic compound represented by the formula (4) as a basic skeleton. The organic compound represented by the formula (4) is symmetrical with respect to both the X axis and the Y axis as shown in formula (6) below.

[Chem. 8]

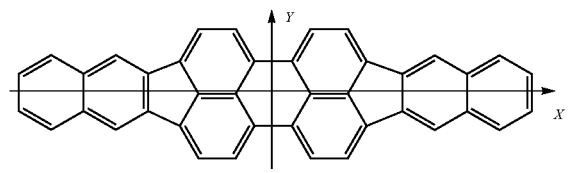

(6)

A compound having high symmetry is considered as a compound having high crystallinity because of easy stacking of molecules. Thus, the compound having high crystallinity is decreased in sublimability. Therefore, the compounds c and d are decreased in sublimability, thereby increasing the temperatures required for sublimation of the compounds. Consequently, sublimation of the compounds c and d is accompanied with decomposition (thermal decomposition).

On the other hand, the compound e shown in Table 2 is a compound having an organic compound represented by the formula (5) as a basic skeleton. The organic compound represented by the formula (5) has no symmetry with respect to both the X axis and the Y axis as shown in formula (7) below.

[Chem. 9]

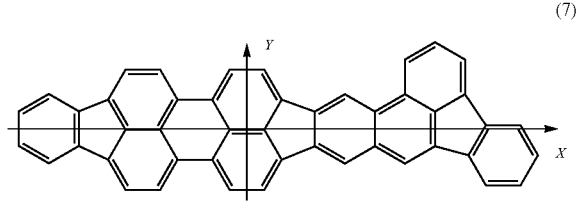

(7)

Therefore, the compound e has suppressed crystallinity and thus can be sublimated at a temperature lower than the compounds c and d without being accompanied with decomposition during sublimation. Thus, the organic compound of the present invention can be purified by sublimation and has the advantage that impurities such as decomposition products are little contained in a light-emitting element. Therefore, the original element performance of a material can be exhibited.

On the other hand, in the compounds shown in Table 2, particularly the compounds c and d, the crystallinity of the molecule can be suppressed to some extent by further introducing a substituent. However, in the compounds shown in Table 2, particularly the compounds b, c, d, and e having a skeleton which emits red light, the molecular weight is further increased by introducing a substituent because these compounds have high molecular weights. Thus, the compounds are highly likely to be thermally decomposed by sublimation purification. Therefore, it is difficult to introduce a substituent effective for suppressing crystallinity.

Since the organic compound according to the present invention has two five-membered ring structures in its skeleton, the compound has a low HOMO (Highest Occupied Molecular Orbital) energy level. This represents that the compound has a low oxidation potential. Therefore, the organic compound according to the present invention is stable to oxidation.

In addition, the organic compound according to the present invention has the basic skeleton free from a heteroatom such as a nitrogen atom. This also contributes to the low oxidation potential of the compound and is a reason why the organic compound according to the present invention is stable to oxidation.

The basic skeleton of the organic compound according to the present invention has a low HOMO energy level. That is, the basic skeleton of the organic compound according to the present invention also has a low LUMO (Lowest Unoccupied Molecular Orbital) energy level.

Examples of the organic compound according to the present invention are given below. However, the present invention is not limited to these examples.

[Chem. 10]

A1

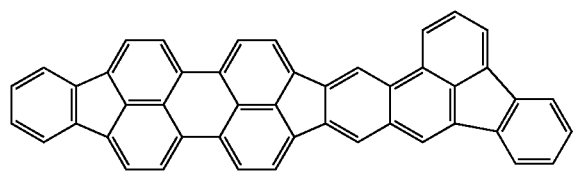

A2

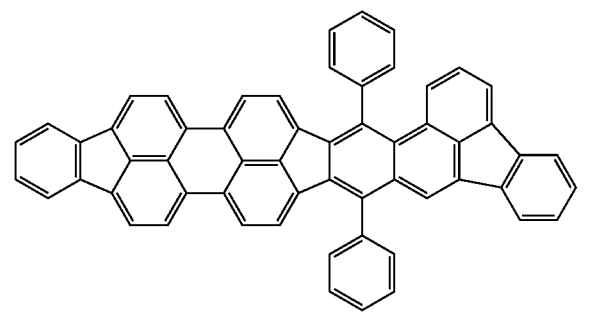

-continued
A3
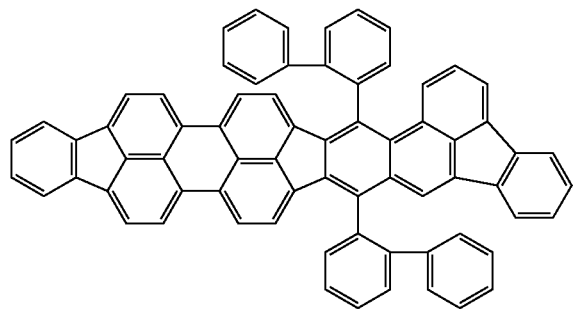
A4
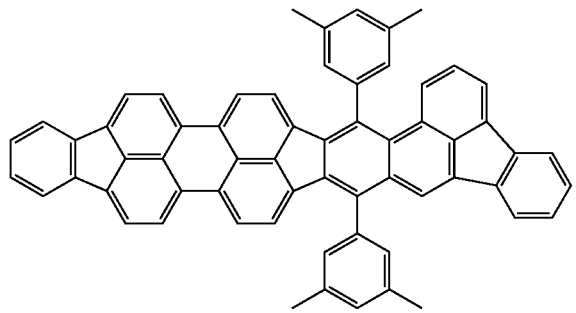
A5
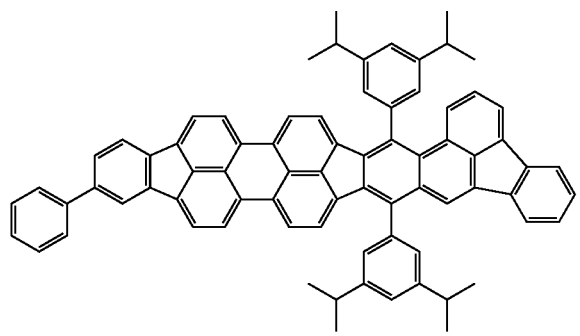
A6
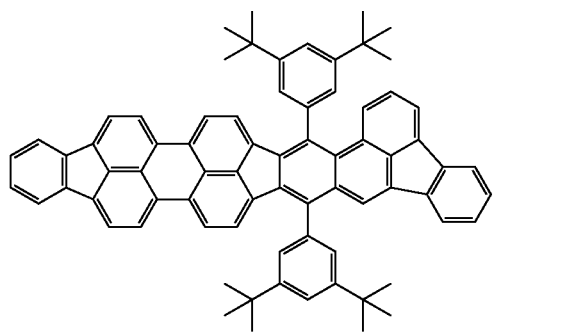
A7
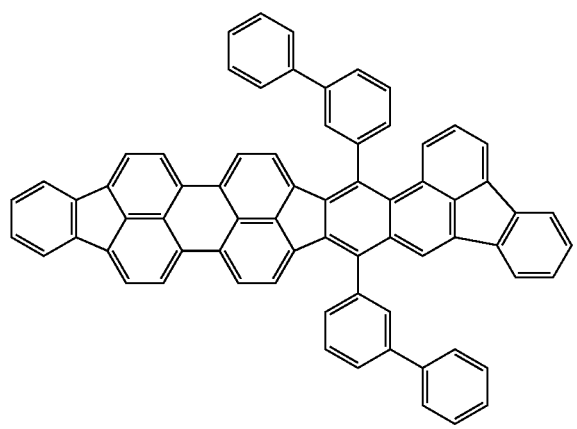
A8
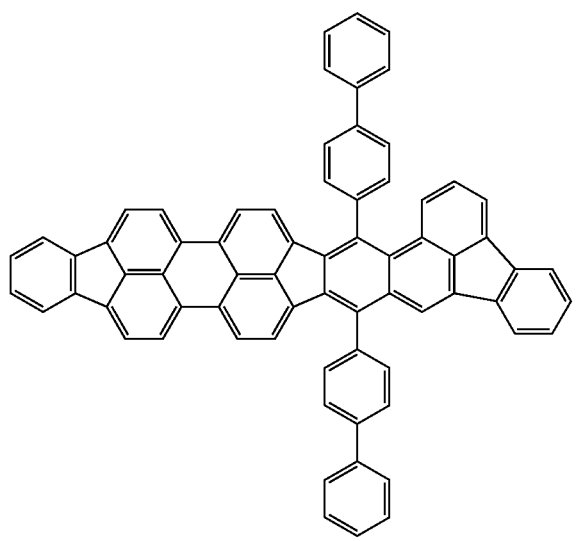
A9
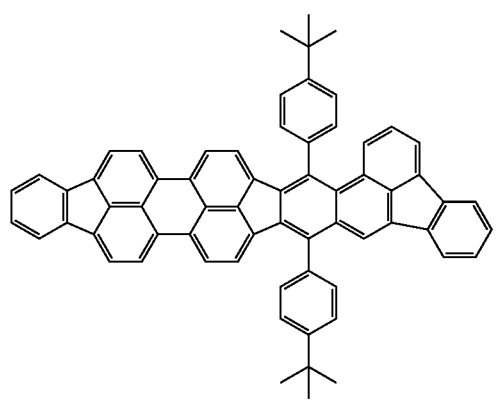
A10
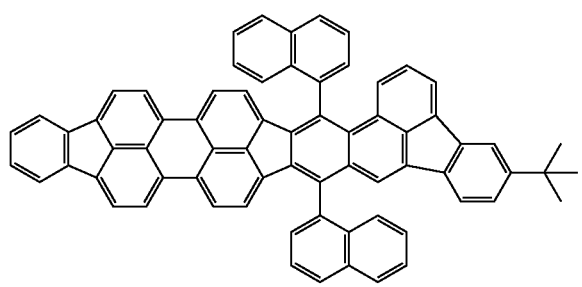

-continued
A11
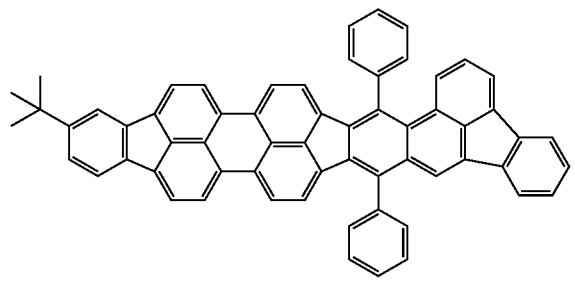
A12
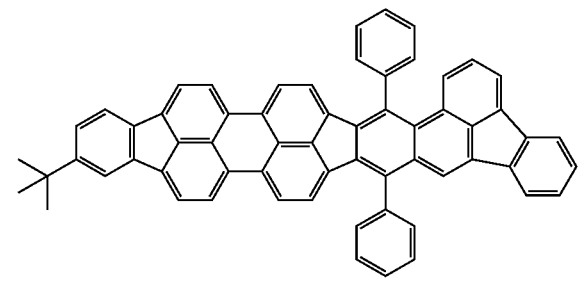
A13
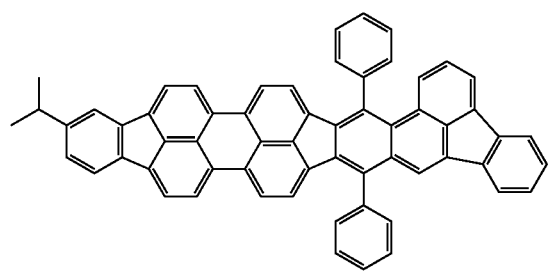
A14
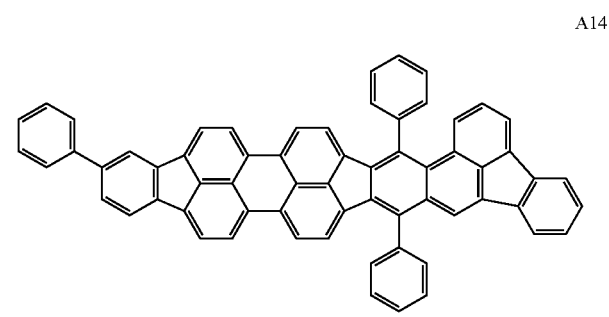
A15
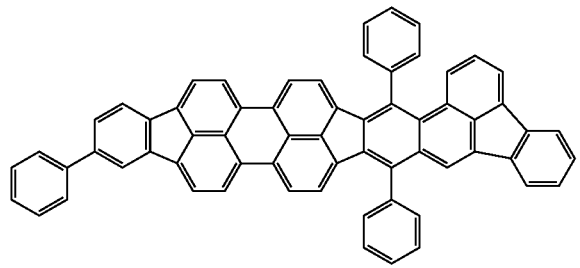
A16
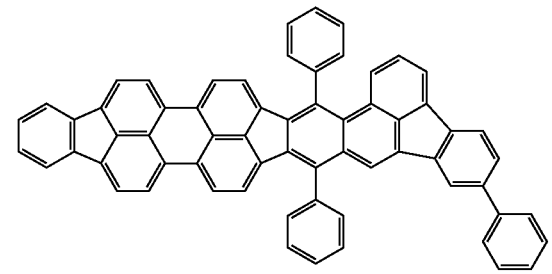
A17
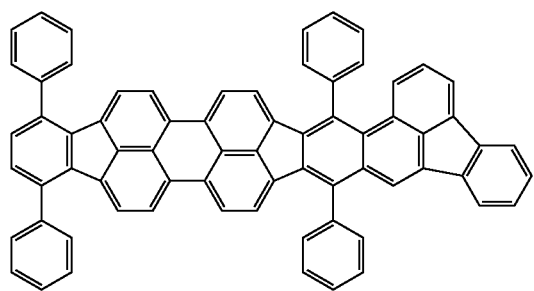
A18
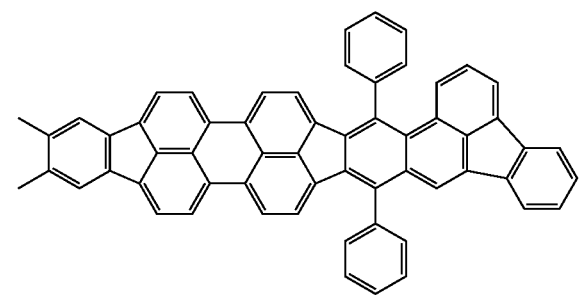
[Chem. 11]
A19
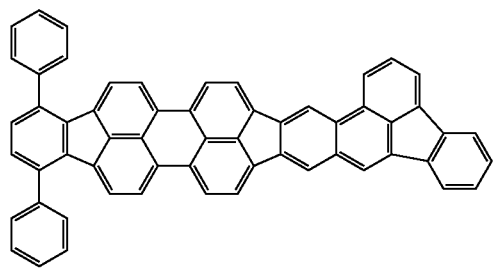
A20
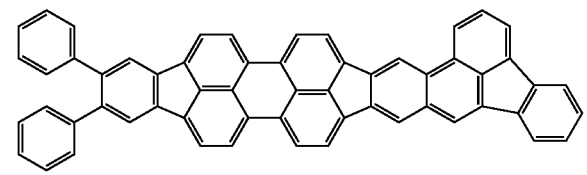

-continued
A21
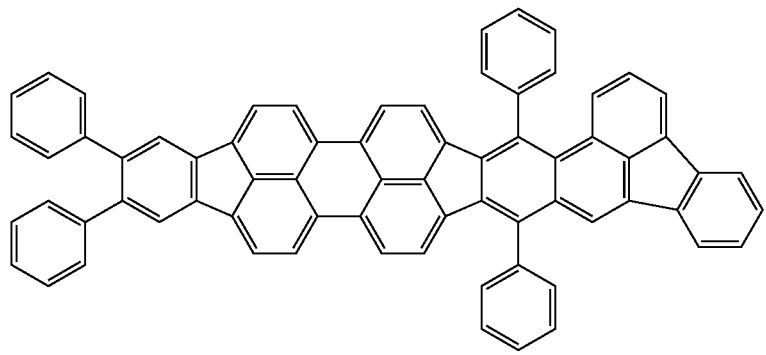
A22
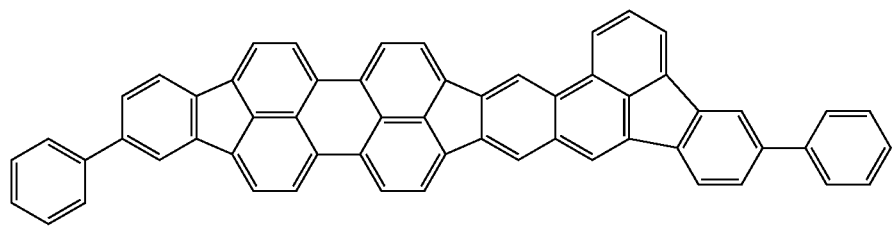
A23
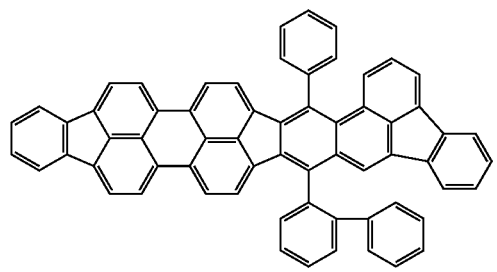
A24
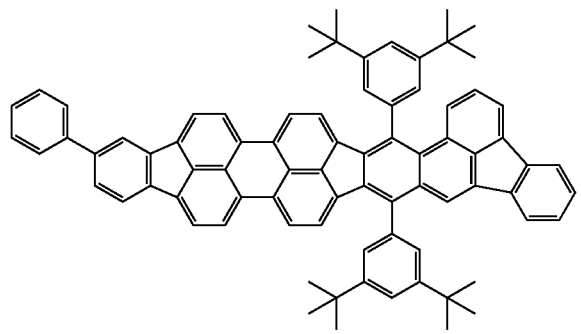
A25
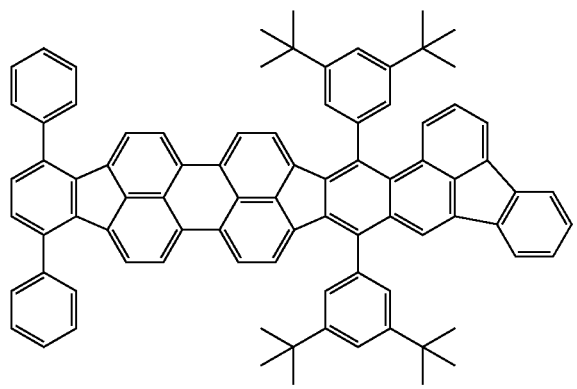
A26
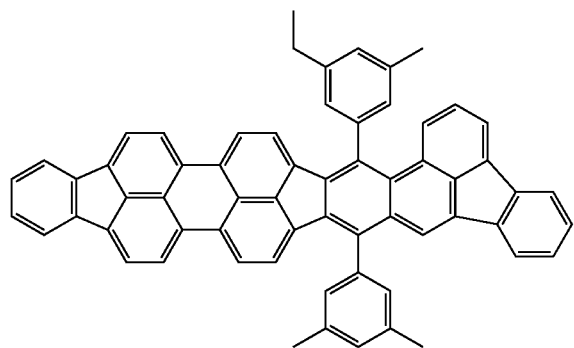
A27
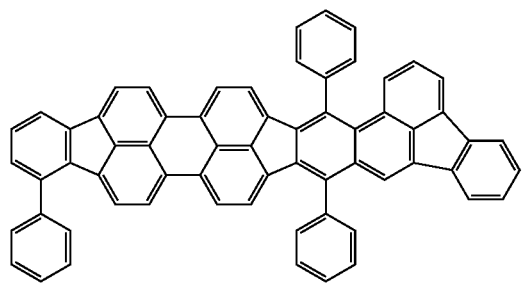
A28
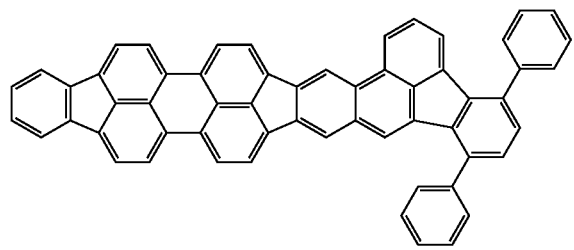

-continued
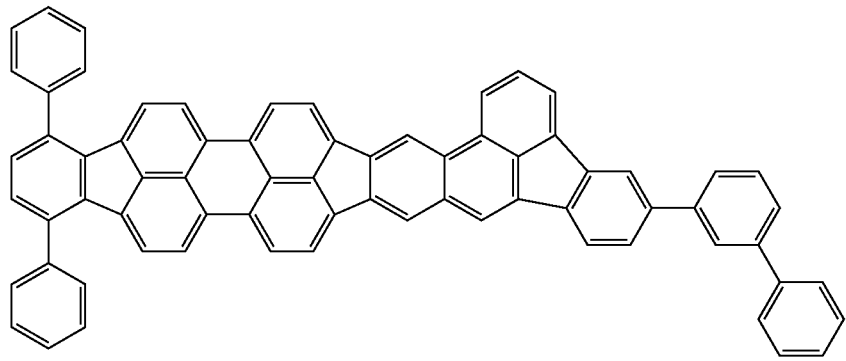
A29
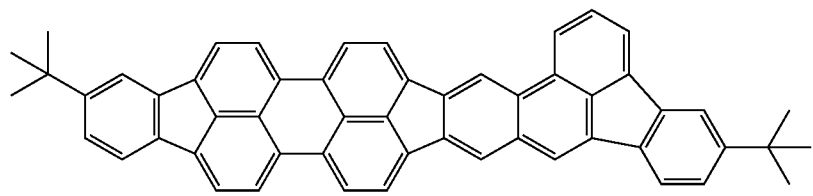
A30
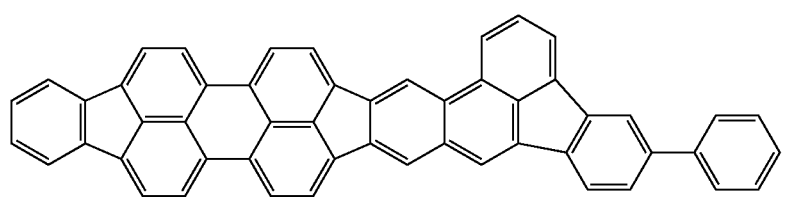
A31
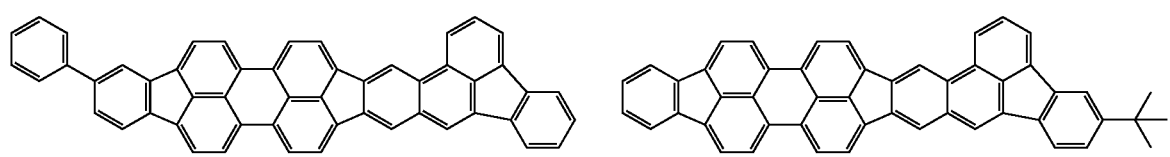
A32            A33
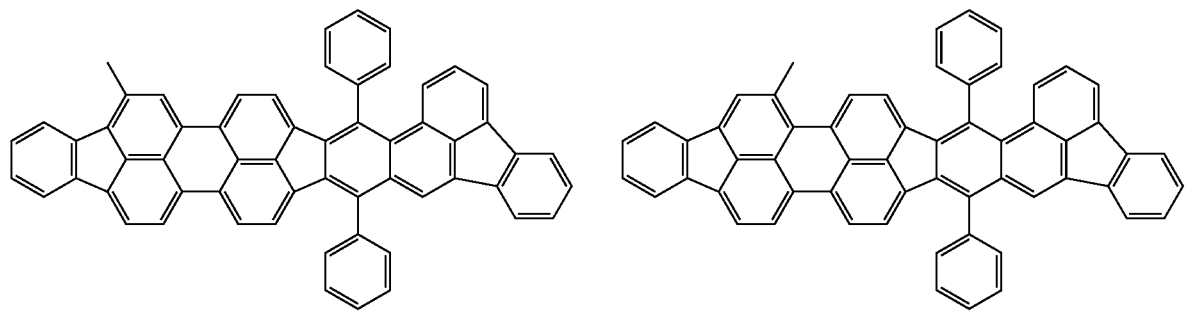
A34            A35
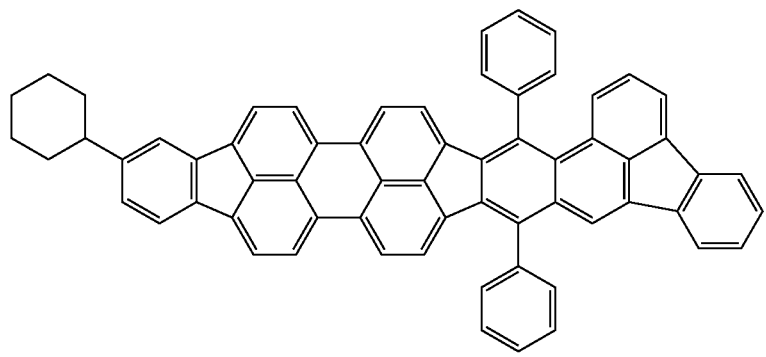
A36

-continued
B1
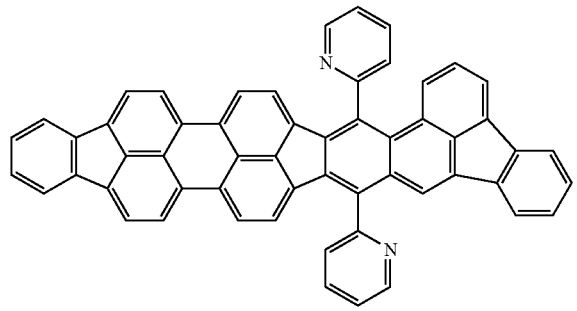
B2
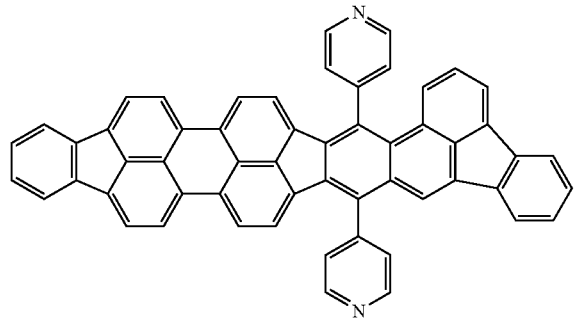
B3
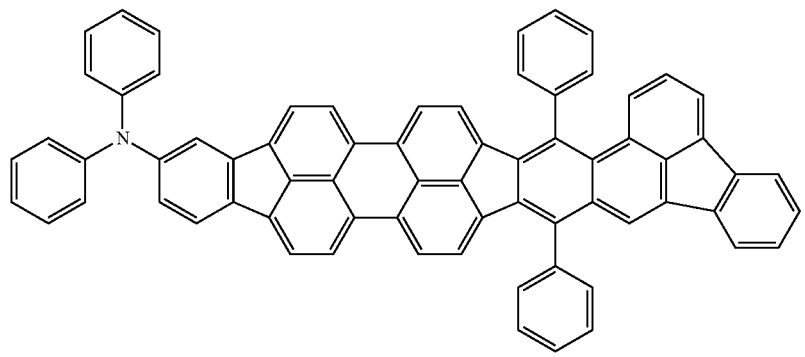
B4
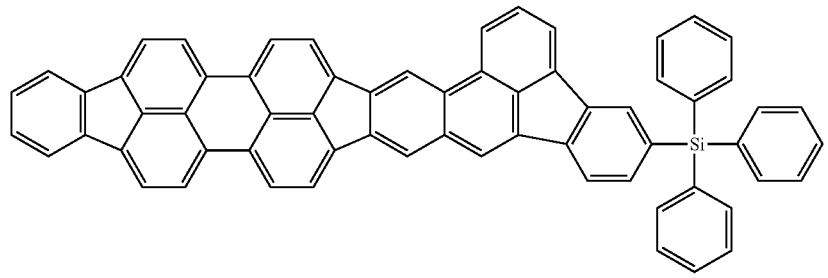
B5
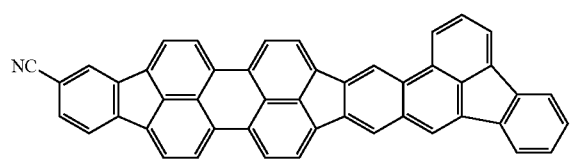
B6
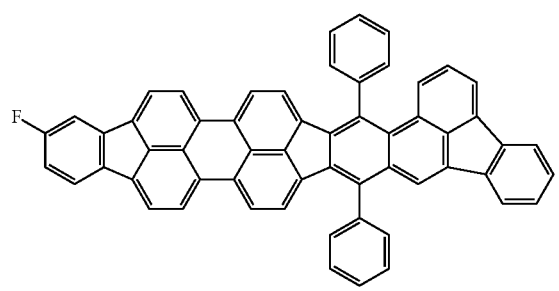
B7
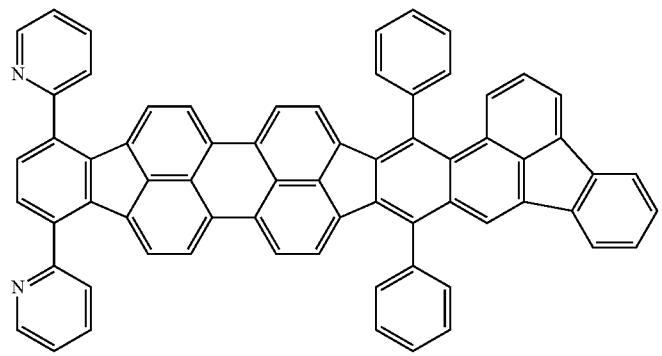

B8

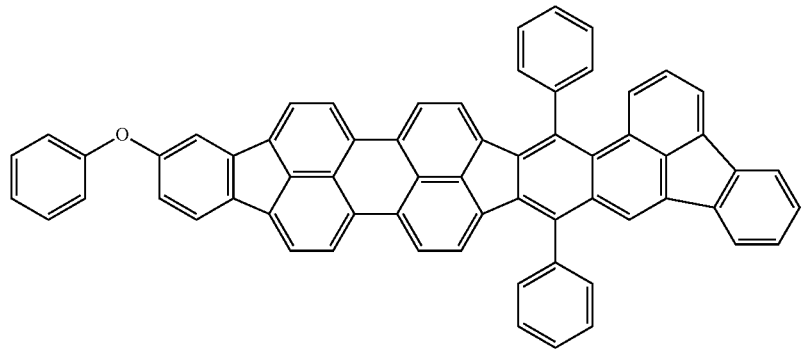

B9

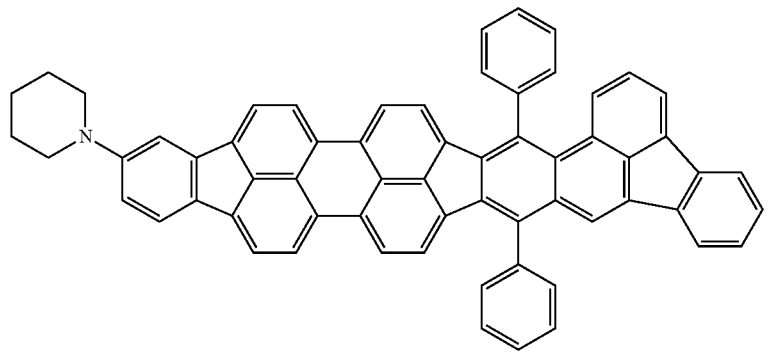

Among the above-described exemplified compounds, the compounds belonging to group A are molecules each entirely composed of only a hydrocarbon. The compounds each composed of only a hydrocarbon generally have a low HOMO energy level. Therefore, the compounds belonging to the group A have a low oxidation potential, which indicates that the organic compounds are stable to oxidation.

Therefore, among organic compounds according to the present invention, organic compounds composed of only a hydrocarbon, i.e., compounds belonging to the group A, are desirable because of the high molecular stability.

On the other hand, among the exemplified compounds, the compounds belonging to group B each have a substituent containing a heteroatom. In this case, the oxidation potential of the molecule is significantly changed, or intermolecular interaction is changed. In addition, the compounds in the group B each having a substituent containing a heteroatom are useful as electron transport, hole transport, and hole trapping light-emitting materials. Also, the organic compounds belonging to the group B can be used at a high concentration of 100%.

Next, an organic electroluminescence element according to an embodiment of the present invention is described.

An organic electroluminescence element according to an embodiment of the present invention includes at least a pair of electrodes, i.e., an anode and a cathode, and an organic compound layer disposed between the electrodes. In the organic electroluminescence element of the present invention, the organic compound layer may be a single layer or a laminate including a plurality of layers as long as it has a light-emitting layer.

When the organic compound layer is a laminate including a plurality of layers, the organic compound layer may include, other than the light-emitting layer, a hole injection layer, a hole transport layer, an electron blocking layer, a hole-exciton blocking layer, an electron transport layer, an electron injection layer, and the like. In addition, the light-emitting layer may be a single layer or a laminate including a plurality of layers.

In the organic electroluminescence element according to the embodiment, at least one of the organic compound layers contains the organic compound according to the present invention. Specifically, any one of the above-described light-emitting layer, hole injection layer, hole transport layer, electron blocking layer, hole-exciton blocking layer, electron transport layer, and electron injection layer contains the organic compound according to the present invention. The light-emitting layer can contain the organic compound according to the present invention.

In the organic electroluminescence element according to the embodiment, when the light-emitting layer contains the organic compound according to the present invention, the light-emitting layer may be a layer containing only the organic compound according to the present invention or a layer containing the organic compound according to the present invention and another compound. When the light-emitting layer is a layer including the organic compound according to the present invention and another compound, the organic compound according to the present invention may be used as a host or a guest of the light-emitting layer. Alternatively, the organic compound may be used as an assist material which can be contained in the light-emitting layer.

The host is a compound having the highest weight ratio among the compounds constituting the light-emitting layer. In addition, the guest is a compound which has a lower weigh ratio than the host among the compounds constituting the light-emitting layer and which mainly contributes to light emission. The assist material is a compound which has a lower weight ratio than the host among the compounds constituting the light-emitting layer and which assists light emission of the guest. In addition, the assist material is also called a "second host".

Here, when the organic compound according to the present invention is used as the guest in the light-emitting layer, the concentration of the guest is preferably 0.01% by weight or more and 20% by weight or less, more preferably 0.2% by weight or more and 5% by weight or less, relative to the total of the light-emitting layer.

When the organic compound according to the present invention is used as the guest in the light-emitting layer, a material having a higher LUMO level (having a LUMO level closer to the vacuum level) than the organic compound according to the present invention can be used as the host. This is because when a material having a higher LUMO level than that of the organic compound according to the present invention is used as the host, the organic compound according to the present invention can more satisfactorily receive electrons supplied to the host in the light-emitting layer because of the lower LUMO level of the organic compound according to the present invention.

As a result of various investigations, the inventors found that when the organic compound according to the present invention is used as the host or guest of the light-emitting layer, particularly the guest of the light-emitting layer, an element having a high efficiency, high luminance, high optical output, and very high durability can be produced. This is described in detail below in examples.

On the other hand, the organic compound according to the present invention can be used as a constituent material of an organic compound layer other than the light-emitting layer constituting the organic electroluminescence element of the present invention. Specifically, the organic compound may be used as a constituent material of the electron transport layer, the electron injection layer, the hole transport layer, the hole injection layer, the hole blocking layer, or the like. In this case, the luminescent color of the organic electroluminescence element is not limited to red. More specifically, the luminescent color may be white or a medium color.

Besides the organic compound according to the present invention, if required, a known low-molecular or high-molecular hole injecting compound or hole transport compound, a compound serving as the host, a light-emitting compound, an electron injecting compound or electron transport compound, and the like can be used together.

Examples of these compounds are given below.

As the hole injecting compound or the hole transport compound, a material having high hole mobility can be used. Examples of a low-molecular or high-molecular material having the hole injecting performance or hole transport performance include, but of course not limited to, triarylamine derivatives, phenylenediamine derivatives, stilbene derivatives, phthalocyanine derivatives, porphyrin derivatives, poly(vinylcarbazole), poly(thiophene), and other conductive polymers.

Examples of the host include compounds shown in Table 3 below.

TABLE 3

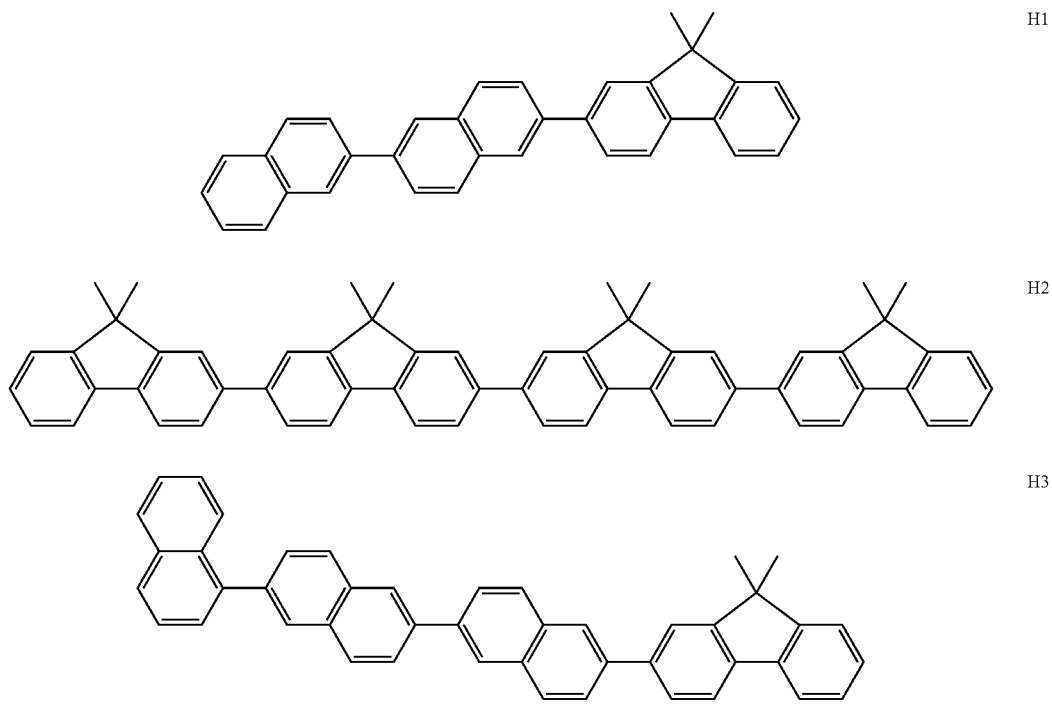

TABLE 3-continued
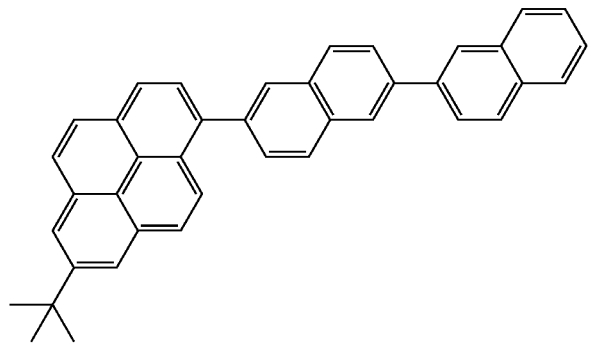 [SMILES: CC(C)(C)c1cc2ccc3ccc(-c4ccc5cc(-c6ccc7ccccc7c6)ccc5c4)c4ccc(c1)c2c34]
H4
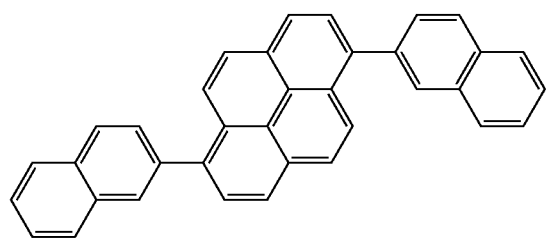 [SMILES: c1ccc2cc(-c3ccc4ccc5c(-c6ccc7ccccc7c6)ccc6ccc3c4c65)ccc2c1]
H5
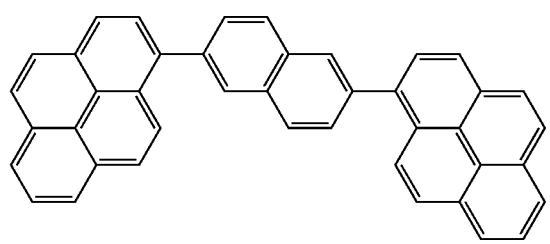 [SMILES: c1cc2ccc3ccc(-c4ccc5cc(-c6ccc7ccc8cccc9ccc6c7c89)ccc5c4)c4ccc(c1)c2c34]
H6
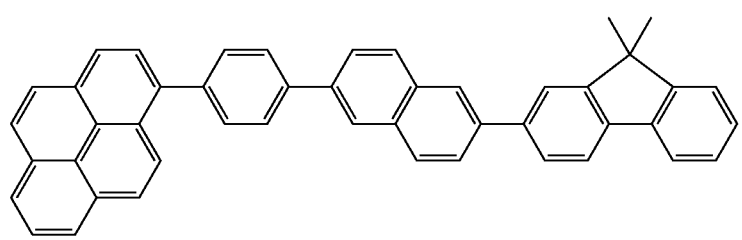 [SMILES: CC1(C)c2ccccc2-c2ccc(-c3ccc4cc(-c5ccc(-c6ccc7ccc8cccc9ccc6c7c89)cc5)ccc4c3)cc21]
H7
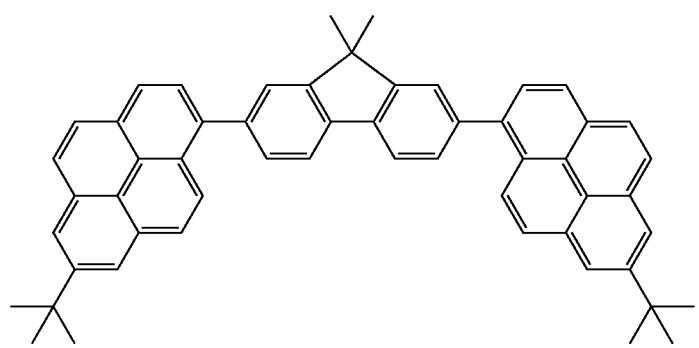 [SMILES: CC(C)(C)c1cc2ccc3ccc(-c4ccc5c(c4)C(C)(C)c4cc(-c6ccc7ccc8cc(C(C)(C)C)cc9ccc6c7c89)ccc4-5)c4ccc(c1)c2c34]
H8

TABLE 3-continued
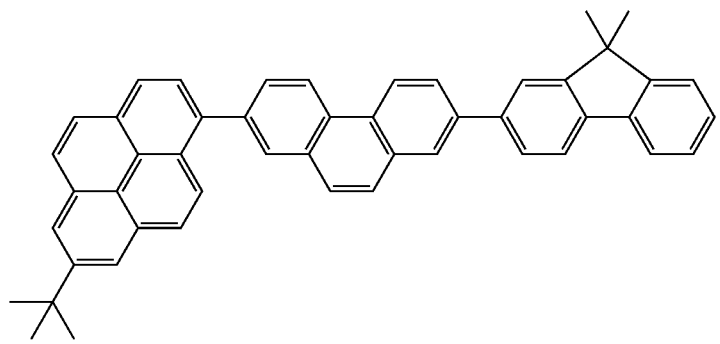 [SMILES: CC(C)(C)c1cc2ccc3ccc(-c4ccc5c(ccc6cc(-c7ccc8c(c7)C(C)(C)c7ccccc7-8)ccc65)c4)c4ccc(c1)c2c34]
H9
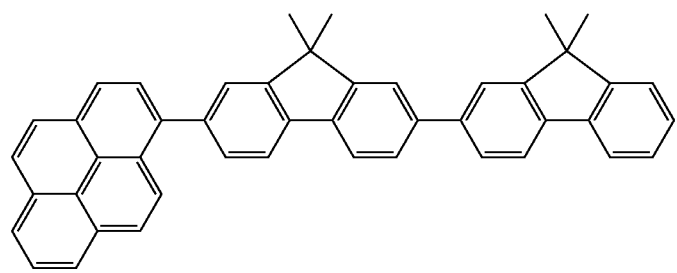 [SMILES: CC1(C)c2ccccc2-c2ccc(-c3ccc4c(c3)C(C)(C)c3cc(-c5ccc6ccc7cccc8ccc5c6c78)ccc3-4)cc21]
H10
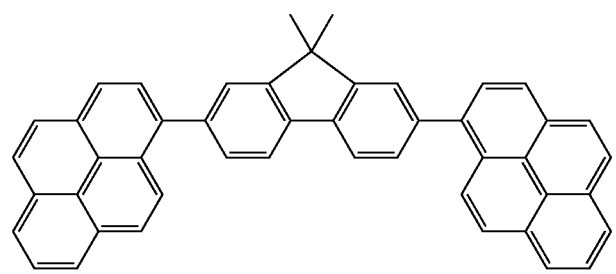 [SMILES: CC1(C)c2cc(-c3ccc4ccc5cccc6ccc3c4c56)ccc2-c2ccc(-c3ccc4ccc5cccc6ccc3c4c56)cc21]
H11
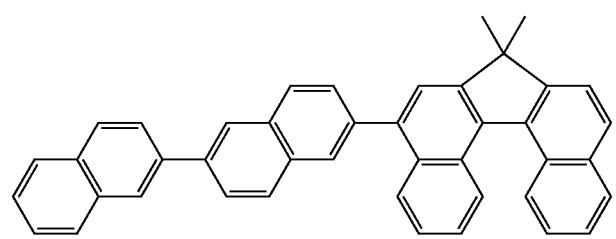 [SMILES: CC1(C)c2ccc3ccccc3c2-c2c1cc(-c1ccc3cc(-c4ccc5ccccc5c4)ccc3c1)c1ccccc21]
H12
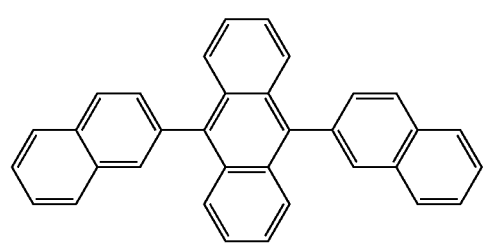 [SMILES: c1ccc2cc(-c3c4ccccc4c(-c4ccc5ccccc5c4)c4ccccc34)ccc2c1]
H13
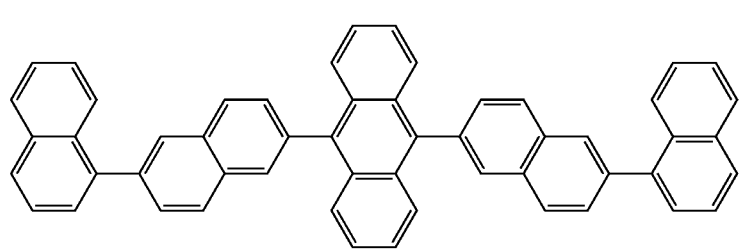 [SMILES: c1ccc2c(-c3ccc4cc(-c5c6ccccc6c(-c6ccc7cc(-c8cccc9ccccc89)ccc7c6)c6ccccc56)ccc4c3)cccc2c1]
H14

TABLE 3-continued
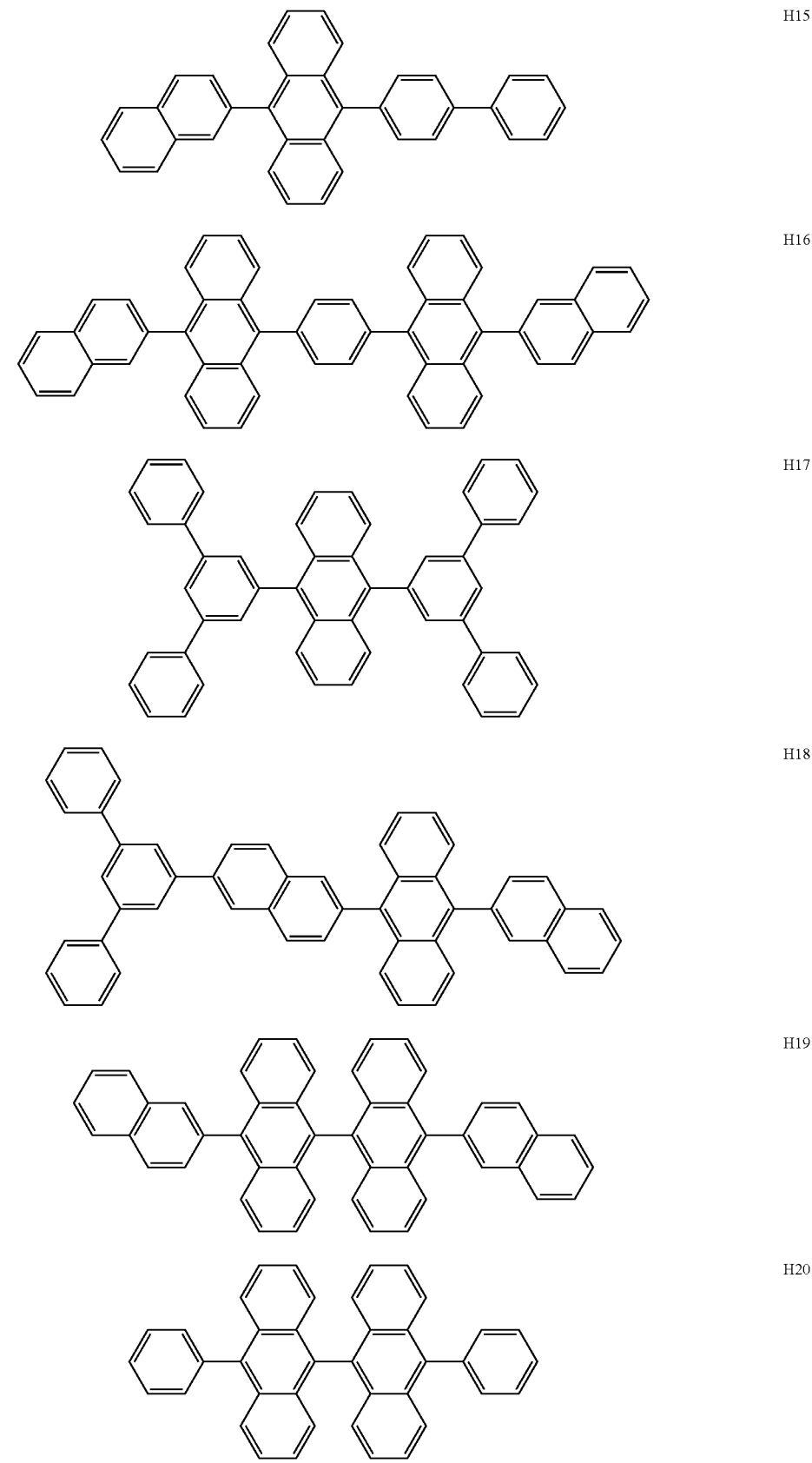
H15
H16
H17
H18
H19
H20

TABLE 3-continued

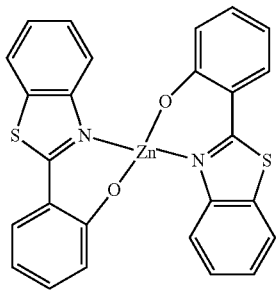

H21

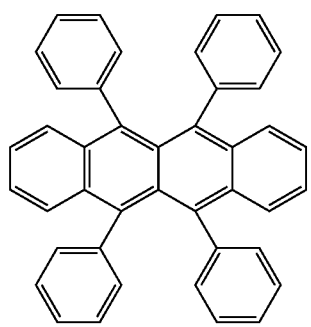 [SMILES: c1ccc(-c2c3ccccc3c(-c3ccccc3)c3c(-c4ccccc4)c4ccccc4c(-c4ccccc4)c23)cc1]

H22

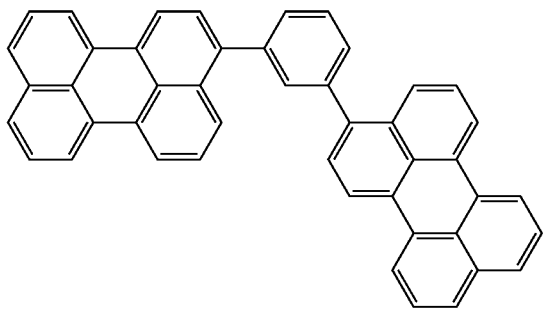 [SMILES: c1cc(-c2ccc3c4cccc5cccc(c6cccc2c63)c54)cc(-c2ccc3c4cccc5cccc(c6cccc2c63)c54)c1]

H23

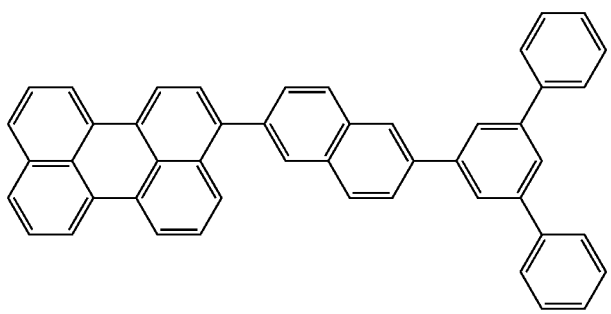 [SMILES: c1ccc(-c2cc(-c3ccccc3)cc(-c3ccc4cc(-c5ccc6c7cccc8cccc(c9cccc5c96)c87)ccc4c3)c2)cc1]

H24

However, the present invention is not limited to these examples. Compounds which are derivatives of the compounds shown in Table 3 can also be used as the host. Other examples include, but of course not limited to, fused-ring compounds (for example, fluorene derivatives, naphthalene derivatives, anthracene derivatives, pyrene derivatives, carbazole derivatives, quinoxaline derivatives, quinoline derivatives, and the like); organic aluminum complexes such as tris(8-quinolinolate) aluminum and the like; organic zinc complexes; triphenylamine derivatives; and polymer derivatives such as poly(fluorene) derivatives, poly(phenylene) derivatives, and the like.

The electron injecting compound and the electron transport compound are appropriately selected in consideration of a balance with the hole mobility of the hole injecting compound and the hole transport compound. Examples of compounds having the electron injecting performance or electron transport performance include, but of course not limited to, oxadiazole derivatives, oxazole derivatives, pyrazine derivatives, triazole derivatives, triazine derivatives, quinoline derivatives, quinoxaline derivatives, phenanthroline derivatives, organic aluminum complexes, and the like.

As a constituent material of the anode, a material having as a large work function as possible can be used. Examples of such a material include elemental metals such as gold, platinum, silver, copper, nickel, palladium, cobalt, selenium, vanadium, tungsten, and the like; alloys each composed of a combination of two or more of these elemental metals; and metal oxides such as tin oxide, zinc oxide, indium oxide, indium tin oxide, (ITO), indium zinc oxide, and the like. Also, conductive polymers such as polyaniline, polypyrrole, polythiophene, and the like may be used. These electrode materials may be used alone or in combination of two or more. Further, the anode may include a single layer or multiple layers.

On the other hand, as a constituent material of the cathode, a material having a small work function can be used. Examples of such a material include alkali metals such as lithium and the like; alkaline-earth metals such as calcium and the like; and elemental metals such as aluminum, titanium, manganese, silver, lead, chromium, and the like. Also, alloys each including a combination of two or more of these elemental metals can be used. Examples of the alloys include magnesium-silver, aluminum-lithium, aluminum-magnesium, and the like. Metal oxides such as indium tin oxide (ITO) can also be used. These electrode materials may be used alone or in combination of two or more. Further, the cathode may include a single layer or multiple layers.

In the organic electroluminescence element according to the embodiment, the layer containing the organic compound according to the present invention and layers containing other organic compounds are formed by a method described below. In general, a thin film is formed by a vacuum deposition method, an ionic vapor deposition method, sputtering, plasma, or a known application method using a solution in a proper solvent (for example, spin coating, dipping, a casting method, a LB method, or an ink jet method). A layer formed by the vacuum deposition or solution application method causes little crystallization and has excellent time stability. In addition, the application method can form a film in combination with an appropriate binder resin.

Examples of the binder resin include, but are not limited to, polyvinylcarbazole resins, polycarbonate resins, polyester resins, ABS resins, acrylic resins, polyimide resins, phenol resins, epoxy resins, silicone resins, urea resins, and the like. These binder resins may be used alone as a homopolymer or a copolymer or used as a mixture of two or more. Further, if required, additives such as a known plasticizer, antioxidant, ultraviolet absorber, and the like may be combined.

The organic electroluminescence element according to the embodiment can be used as a component member of a display device or an illuminating device. Other applications include an exposure light source of an electrophotographic image forming apparatus, a back light of a liquid crystal display device, and the like.

The above-described display device includes the organic electroluminescence element of the present invention in a display portion. The display portion includes a plurality of pixels. Each of the pixels includes the organic electroluminescence element of the present invention and a TFT element as an example of a switching element for controlling luminance, the anode or cathode of the organic electroluminescence element being electrically connected to a drain electrode or source electrode of the TFT element. In this case, the display device can be used as an image display device for PC (Personal Computer).

The display device may be an image input device including an input portion to which image information is input from area CCD (Charge-Coupled Device), linear CCD, a memory card, or the like, so that the input image is output to the display portion. In addition, the display device may be used both as a display portion which is provided in an imaging apparatus or an ink jet printer and which has the image output function of displaying the image information input from the outside and as an operational panel having the input function of inputting processing information for the image. Further, the display device may be used in a display portion of a multifunction printer.

Next, a display device using the organic electroluminescence element according to the embodiment of the present invention is described with referent to FIG. 1.

FIG. 1 is a schematic sectional view showing an example of a display device including the organic electroluminescence element according to the embodiment of the present invention and a TFT element as an example of a switching element electrically connected to the organic electroluminescence element. In a display device 20 shown in FIG. 1, two pairs of the organic electroluminescence elements and the TFT elements are shown in the FIGURE. The structure is described in detail below.

The display device 20 shown in FIG. 1 is provided with a substrate 1 of glass or the like and a moisture-proofing film 2 provided on the substrate 1 in order to protect the TFT elements or the organic layers. In addition, reference numeral 3 denotes a metal gate electrode, reference numeral 4 denotes a gate insulating film, and reference numeral 5 denotes a semiconductor layer.

A TFT element 8 includes the semiconductor layer 5, a drain electrode 6, and a source electrode 7. An insulating film 9 is provided on the TFT element 8. An anode 11 of the organic electroluminescence element is connected to the source electrode 7 through a contact hole 10. The configuration of the display device is not limited to this as long as any one of the anode and the cathode is connected to any one of the source electrode and the drain electrode of the TFT element.

In the display device 20 shown in FIG. 1, an organic compound layer 12 is shown as a single layer regardless of being a single layer or a multilayer organic compound layer. In addition, a first protective layer 14 and a second protective layer 15 are provided on the cathode 13 in order to suppress deterioration of the organic electroluminescence element.

In the display device of the present invention, a switching element is not particularly limited, but a single crystal silicon substrate and a MIM element or an a-Si element may be used.

EXAMPLES

The present invention is described below with reference to examples. However, the present invention is not limited to these examples.

Example 1
Synthesis of Exemplified Compound A2
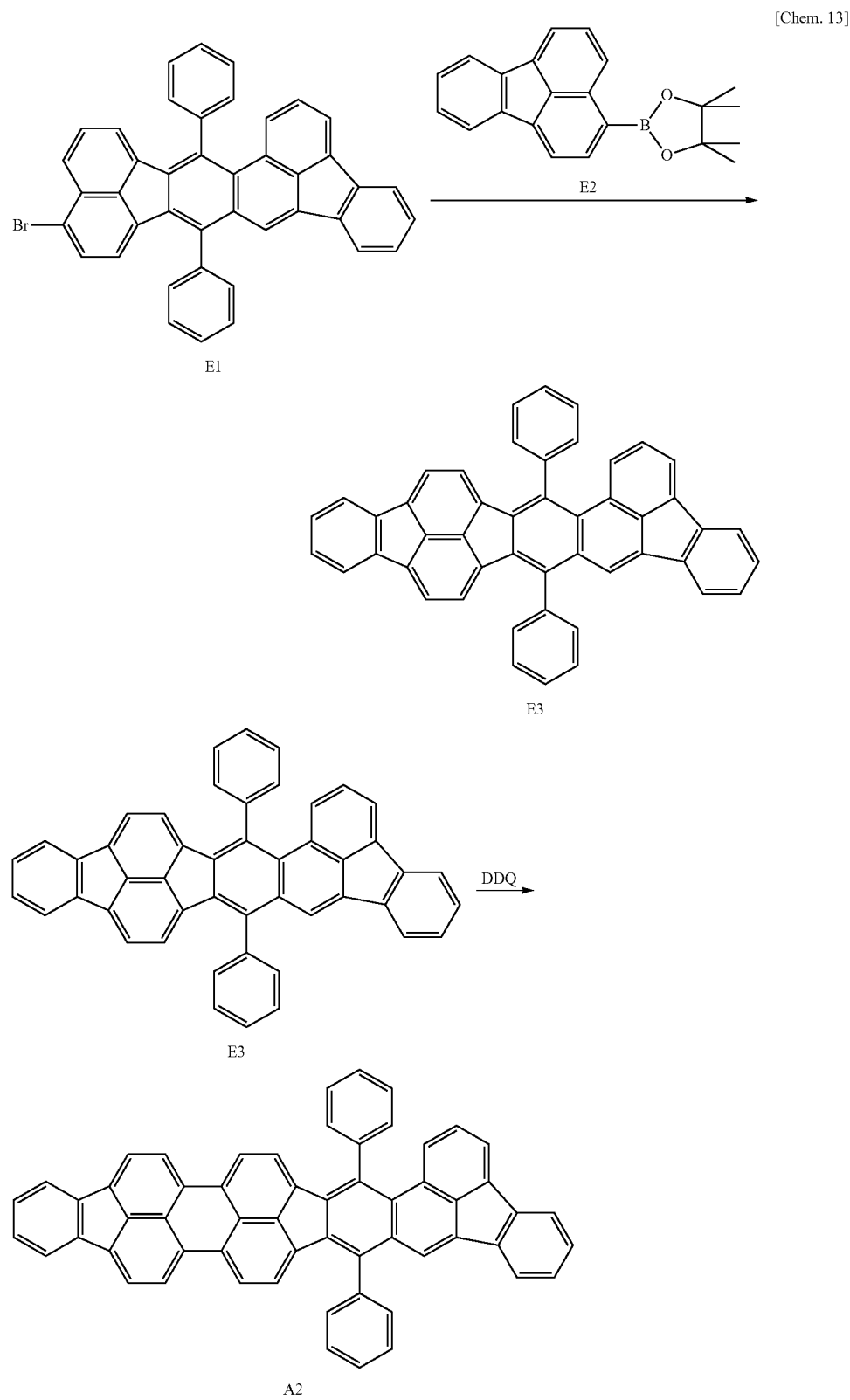
[Chem. 13]

(1) Synthesis of Compound E3

Reagents and solvents described below were placed in a 100 ml recovery flask. Compound E1 below is a compound synthesized on the basis of Japanese Patent Laid-Open No. 2010-254610.

Compound E1: 606 mg (1 mmol)
Compound E2: 327 mg (1 mmol)
Pd(PPh$_3$)$_4$: 0.02 g
Toluene: 10 ml
Ethanol: 5 ml
2M-aqueous sodium carbonate solution: 10 ml Next, the reaction solution was heated to 80° C. and then stirred at this temperature (80° C.) for 8 hours. After the completion of reaction, crystals were filtered off and dispersed and washed in order with water, ethanol, and heptane. Next, the resultant crystals were dissolved in toluene by heating and then purified by column chromatography (toluene/heptane=1:3) and then recrystallized with chloroform/methanol to produce 583 mg of compound E3 as yellow crystals (yield: 80%).

(2) Synthesis of Exemplified Compound A2

In a reactor, 218 mg (0.3 mmol) of compound E3 was placed and then dissolved in 10 ml of methylene chloride. Next, regents below were placed in the reactor in a water bath.

Trifluoroacetic acid: 2 ml
BF$_3$.OEt: 1.8 ml

Next, the reaction solution was stirred for about 10 minutes, and then 136 mg (0.6 mmol) of DDQ was slowly added to the solution. Next, the reaction solution was stirred for 4 hours, and then 112 mg (0.6 mmol) of ferrocene was added to the solution. The resultant red precipitates were filtered off to produce a dark-red solid. Next, the solid was dissolved in chlorobenzene by heating, and the resultant hot solution was filtered. The filtrate was recrystallized two times with chlorobenzene/methanol to produce 159 mg of exemplified compound A2 as dark-red crystals (yield: 73%). In addition, 150 mg of the compound A2 was purified by sublimation using a sublimation purification apparatus manufactured by Ulvac Kiko Inc. under conditions described below. As a result of the sublimation purification, 115 mg of exemplified compound A2 was obtained.

Degree of vacuum: 7.0×10$^{-1}$ Pa
Argon gas flow rate: 10 ml/min
Sublimation temperature: 410° C.

As a result of measurement of the purity of the resultant compound with HPLC (High-Performance Liquid Chromatography), the purity was confirmed to be 99% or more.

In addition, an emission spectrum of a 1×10$^{-5}$ mol/L toluene solution of exemplified compound A2 was measured. Specifically, photoluminescence was measured at an excitation wavelength of 520 nm using Hitachi F-4500. As a result, an emission spectrum having a peak intensity at 582 nm was obtained.

In addition, exemplified compound A2 had low solubility in a solvent and was thus difficult to identify by NMR. Therefore, the compound was identified by measuring the molecular weight using JMS-T100TD (DART-TOF-MASS) manufactured by JEOL, Ltd. The result is shown below.

DART-TOF-MASS: M$^+$=727.9

Example 2

Synthesis of Exemplified Compound A3

Exemplified compound A3 was produced by the same method as in Example 1 except that in Example 1(1), compound E4 shown below was used in place of compound E1.

[Chem. 14]

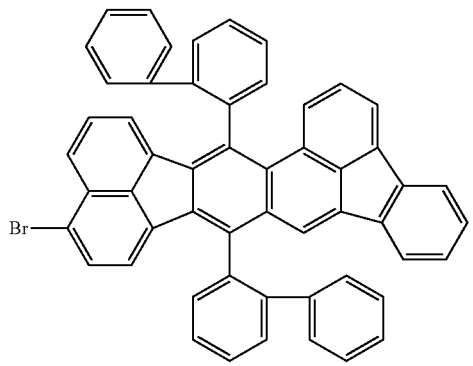

E4

As a result of measurement of the purity of the resultant compound with HPLC, the purity was confirmed to be 99.5% or more.

In addition, an emission spectrum of a toluene solution (concentration: 1×10$^{-5}$ mol/L) of exemplified compound A3 was measured by the same method as in Example 1. As a result, an emission spectrum having a peak intensity at 583 nm was obtained.

Further, the compound was identified by measuring the molecular weight using JMS-T100TD (DART-TOF-MASS) manufactured by JEOL, Ltd.

DART-TOF-MASS: M$^+$=879.3

Example 3

Synthesis of Exemplified Compound A6

Exemplified compound A6 was produced by the same method as in Example 1 except that in Example 1(1), compound E5 shown below was used in place of compound E1.

[Chem. 15]

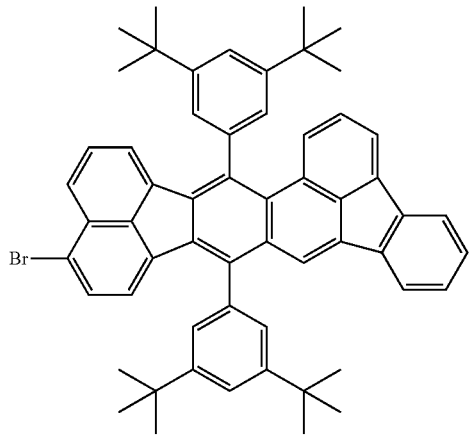

E5

As a result of measurement of the purity of the resultant compound with HPLC, the purity was confirmed to be 99% or more.

In addition, an emission spectrum of a toluene solution (concentration: 1×10$^{-5}$ mol/L) of exemplified compound A6 was measured by the same method as in Example 1. As a result, an emission spectrum having a peak intensity at 590 nm was obtained.

Further, the compound was identified by measuring the molecular weight using JMS-T100TD (DART-TOF-MASS) manufactured by JEOL, Ltd.

DART-TOF-MASS: M$^+$=951.5

Example 4

Synthesis of Exemplified Compound A14

Exemplified compound A14 was produced by the same method as in Example 1 except that in Example 1(1), compound E6 shown below was used in place of compound E2.

[Chem. 16]

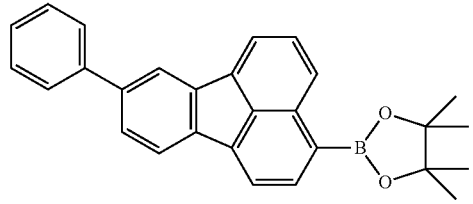

E6

As a result of measurement of the purity of the resultant compound with HPLC, the purity was confirmed to be 99% or more.

In addition, an emission spectrum of a toluene solution (concentration: 1×10$^{-5}$ mol/L) of exemplified compound A14 was measured by the same method as in Example 1. As a result, an emission spectrum having a peak intensity at 590 nm was obtained.

Further, the compound was identified by measuring the molecular weight using JMS-T100TD (DART-TOF-MASS) manufactured by JEOL, Ltd.

DART-TOF-MASS: M$^+$=803.3

Example 5

Synthesis of Exemplified Compound A17

Exemplified compound A17 was produced by the same method as in Example 1 except that in Example 1(1), compound E7 shown below was used in place of compound E2.

[Chem. 17]

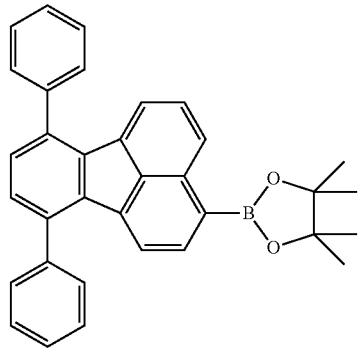

E7

As a result of measurement of the purity of the resultant compound with HPLC, the purity was confirmed to be 99% or more.

In addition, an emission spectrum of a toluene solution (concentration: 1×10$^{-5}$ mol/L) of exemplified compound A17 was measured by the same method as in Example 1. As a result, an emission spectrum having a peak intensity at 590 nm was obtained.

Further, the compound was identified by measuring the molecular weight using JMS-T100TD (DART-TOF-MASS) manufactured by JEOL, Ltd.

DART-TOF-MASS: M$^+$=879.3

Example 6

In this example, an organic electroluminescence element was produced, in which an anode, a hole transport layer, a light-emitting layer, a hole-exciton blocking layer, an electron transport layer, and a cathode were sequentially formed on a substrate. Some of the materials used in the example are shown below.

[Chem. 18]

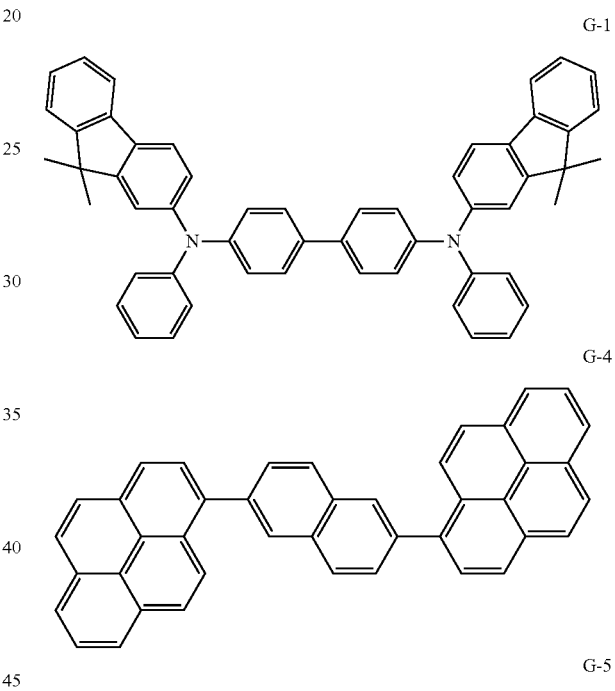

First, ITO was deposited on a glass substrate and subjected to desired patterning to form an ITO electrode (anode). In this case, the thickness of the ITO electrode was 100 nm. The substrate including the ITO electrode formed as described above was used as an ITO substrate in a subsequent step.

Next, organic compound layers and electrode layers shown in Table 4 below were continuously deposited on the ITO substrate by resistance-heating vacuum deposition in a vacuum chamber of 1×10⁻⁵ Pa. In this deposition, the electrode area of a counter electrode (a metal electrode layer, cathode) was 3 mm².

TABLE 4

|  | Material | Thickness [nm] |
|---|---|---|
| Hole transport layer | G-1 | 40 |
| Light-emitting layer | G-2 (host) G-3 (assist material) Exemplified compound A1 (guest) (G-2:G-3:A1 = 60:39:1 (weight ratio) | 30 |
| Hole-exciton blocking layer | G-4 | 10 |
| Electron transport layer | G-5 | 30 |
| First metal electrode layer | LiF | 1 |
| Second metal electrode layer | Al | 100 |

In this example, G-2 and G-3 are H6 and H22, respectively, shown in Table 3.

The characteristics of the resultant element were measured and evaluated. Specifically, a current-voltage characteristic was measured with microammeter 4140B manufactured by Hewlett-Packard Company, and luminance was measured with BM7 manufactured by Topcon Corporation. The results are shown in Table 5.

Examples 7 to 16

Organic electroluminescence elements were produced by the same method as in Example 6 except that G-2, G-3, and the guest in Example 6 were appropriately changed to the compounds shown in Table 5. The characteristics of each of the resultant elements were measured and evaluated by the same method as in Example 6. The results of measurement are shown in Table 5. In Table 5, each of H2, H4, H11, H18, H19, H₂0, H21, and H24 used as G-2, and H23 and H24 used as G-3 was the host shown in Table 3.

TABLE 5

|  | Guest | G-2 | G-3 | Luminous efficiency (cd/A) | Voltage (V) |
|---|---|---|---|---|---|
| Example 6 | A1 | H6 | H22 | 2.5 | 4.1 |
| Example 7 | A2 | H11 | H23 | 3.0 | 4.2 |
| Example 8 | A2 | H19 | H22 | 4.5 | 4.5 |
| Example 9 | A3 | H18 | H24 | 4.3 | 4.3 |
| Example 10 | A5 | H24 | H22 | 3.5 | 4.1 |
| Example 11 | A6 | H11 | H24 | 3.8 | 4.2 |
| Example 12 | A12 | H4 | H22 | 3.2 | 4.5 |
| Example 13 | A14 | H20 | H23 | 4.1 | 4.6 |
| Example 14 | A15 | H2 | H22 | 3.3 | 4.2 |
| Example 15 | A25 | H19 | H22 | 4.3 | 4.2 |
| Example 16 | B1 | H21 | H23 | 2.2 | 4.1 |

Example 17

In this example, an organic electroluminescence element was produced, in which an anode, a hole injection layer, a hole transport layer, a light-emitting layer, an electron transport layer, an electron injection layer, and a cathode were sequentially formed on a substrate. The organic electroluminescence element produced in this example has a resonant structure. Some of the materials used in the example are shown below.

[Chem. 19]

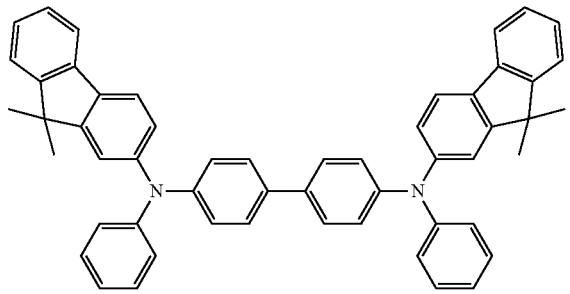

G-11

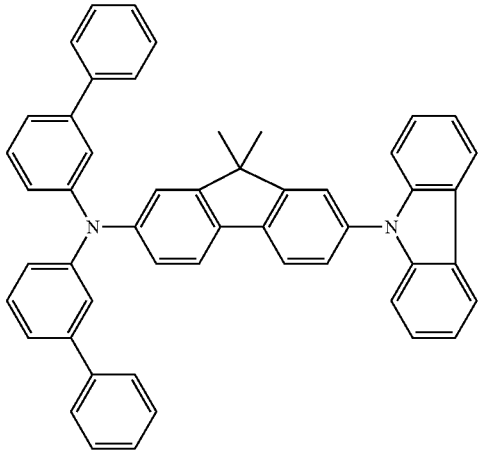

G-12

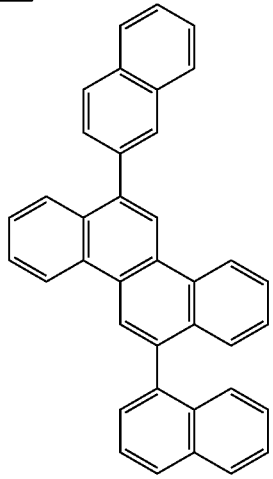

G-14

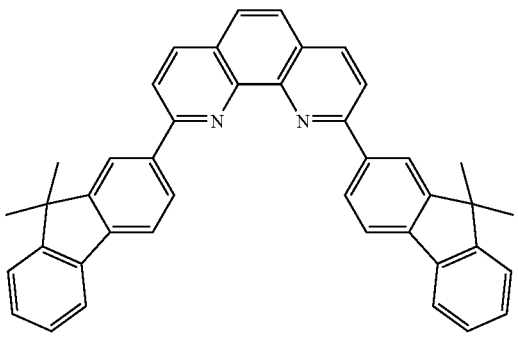

G-15

First, an aluminum alloy (AlNd) was deposited on a glass substrate (support) by sputtering to form a reflective anode. In this case, the thickness of the reflective anode was 100 nm. Next, ITO was deposited on the reflective anode by sputtering to form a transparent anode. The thickness of the transparent anode was 80 nm. Next, an acrylic element separation film was formed in a thickness of 1.5 μm around the anode and then subjected to desired patterning to provide an opening having a radius of 3 mm. Next, the substrate with the anode formed thereon was ultrasonically washed in turn with acetone and isopropyl alcohol (IPA). Next, the substrate was washed by boiling with IPA and then dried. Next, the surface of the substrate was washed with UV/ozone.

Next, the organic compound layers shown in Table 6 below were continuously deposited on the ITO substrate by resistance-heating vacuum deposition in a vacuum chamber of $1 \times 10^{-5}$ Pa.

TABLE 6

| | Material | Thickness [nm] |
|---|---|---|
| Hole injection layer | G-11 | 135 |
| Hole transport layer | G-12 | 10 |
| Light-emitting layer | G-13 (host) | 35 |
| | G-14 (assist material) | |
| | Exemplified compound A2 (guest) | |
| | (G-13:G-14:A2 = 70:29:1 (weight ratio) | |
| Electron transport layer | G-14 | 10 |
| Electron injection layer | G-15 | 70 |
| | Li (G-15:Li = 80:20 (weight ratio) | |

In this example, G-13 and G-14 are H11 and H24, respectively, shown in Table 3.

Next, IZO was deposited on the electron injection layer by sputtering to form the cathode. The thickness of the cathode was 30 nm. Finally, sealing was performed in a nitrogen atmosphere. The organic electroluminescence element was produced as described above.

The characteristics of the resultant element were measured and evaluated. Specifically, a current-voltage characteristic was measured with microammeter 4140B manufactured by Hewlett-Packard Company, and luminance was measured with BM7 manufactured by Topcon Corporation. The results are shown in Table 7.

Examples 18 to 21

Organic electroluminescence elements were produced by the same method as in Example 17 except that G-13, G-14, and the guest in Example 17 were appropriately changed to the compounds shown in Table 7. The characteristics of each of the resultant elements were measured and evaluated by the same method as in Example 17. The results of measurement are shown in Table 7. In Table 7, each of H6, H19, H23, and H24 used as G-13, and H22 and H23 used as G-14 was the host shown in Table 3.

TABLE 7

| | Guest | G-13 | G-14 | Luminous efficiency (cd/A) | Voltage (V) |
|---|---|---|---|---|---|
| Example 17 | A2 | H11 | H24 | 6.2 | 4.6 |
| Example 18 | A3 | H19 | H22 | 6.8 | 4.3 |
| Example 19 | A14 | H23 | H22 | 7.5 | 4.4 |
| Example 20 | A17 | H24 | H22 | 7.3 | 4.6 |
| Example 21 | A24 | H6 | H23 | 7.0 | 4.5 |

Example 22

In this example, an organic electroluminescence element was produced, in which an anode, a hole transport layer, a first light-emitting layer, a second light-emitting layer, a hole-exciton blocking layer, an electron transport layer, and a cathode were sequentially formed on a substrate. The organic electroluminescence element of this embodiment includes a plurality of light-emitting layers and thus has a mode in which the guests contained in the respective light-emitting layers individually or simultaneously emit light. Some of the materials used in the example are shown below.

[Chem. 20]

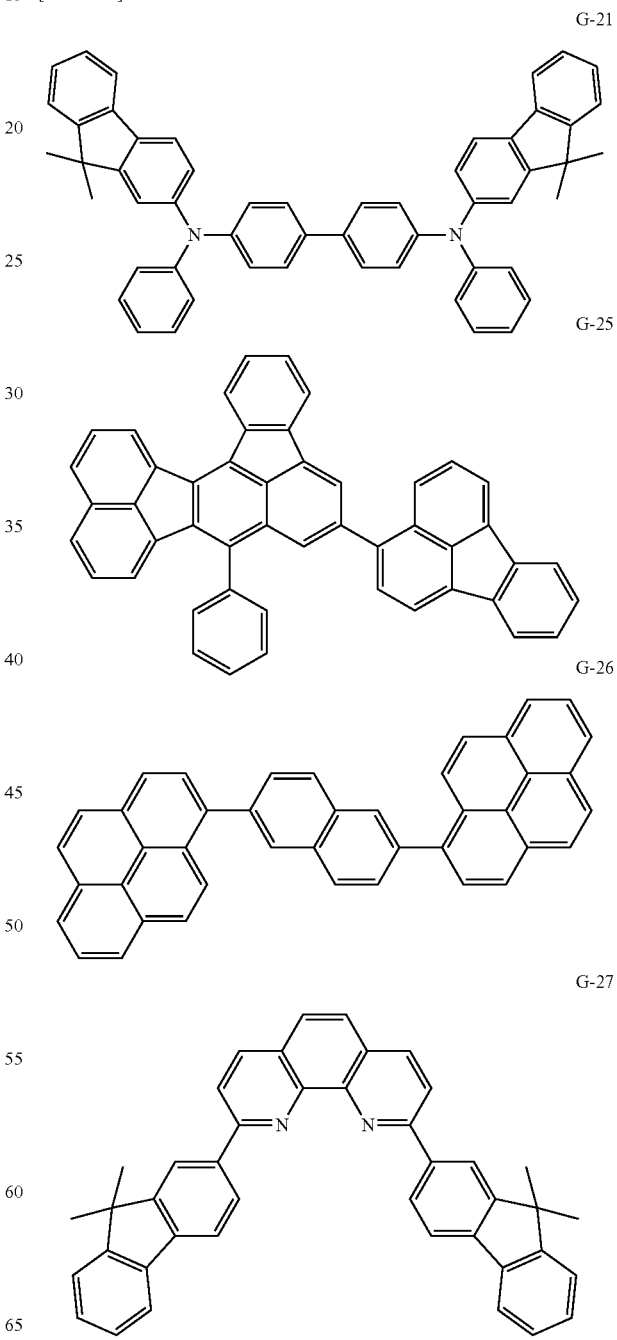

First, ITO was deposited on a glass substrate and subjected to desired patterning to form an ITO electrode (anode). In this case, the thickness of the ITO electrode was 100 nm. The substrate with the ITO electrode formed thereon was used as an ITO substrate in a subsequent step.

Next, the organic compound layers and electrode layers shown in Table 8 below were continuously deposited on the ITO substrate by resistance-heating vacuum deposition in a vacuum chamber of $1 \times 10^{-5}$ Pa. The electrode area of a counter electrode (metal electrode layer, cathode) was 3 mm$^2$.

TABLE 8

| | Material | Thickness [nm] |
|---|---|---|
| Hole transport layer | G-21 | 40 |
| First light-emitting layer | G-22 (first host) G-23 (first assist material) Exemplified compound A2 (first guest) (G-22:G-23:A2 = 60:39:1 (weight ratio) | 30 |
| Second light-emitting layer | G-24 (second host) G-25 (second guest) (G-24:G-25 = 98:2 (weight ratio) | 10 |
| Hole-exciton blocking layer | G-26 | 10 |
| Electron transport layer | G-27 | 30 |
| First metal electrode layer | LiF | 1 |
| Second metal electrode layer | Al | 100 |

In this example, G-22, G-23, and G-24 are H11, H22, and H11, respectively, shown in Table 3.

The characteristics of the resultant element were measured and evaluated. Specifically, a current-voltage characteristic was measured with microammeter 4140B manufactured by Hewlett-Packard Company, and luminance was measured with BM7 manufactured by Topcon Corporation. The results are shown in Table 9.

Examples 23 and 24

Organic electroluminescence elements were produced by the same method as in Example 22 except that G-22, G-23, G-24, and the guest in Example 22 were appropriately changed to the compounds shown in Table 9. The characteristics of each of the resultant elements were measured and evaluated by the same method as in Example 22. The results of measurement are shown in Table 9. In Table 9, each of H18 and H23 used as G-22, H24 used as G-23, and H4 and H15 used as G-24 was the host shown in Table 3.

TABLE 9

| | Guest | G-22 | G-23 | G-24 | Luminous efficiency (cd/A) | Voltage (V) |
|---|---|---|---|---|---|---|
| Example 22 | A2 | H11 | H22 | H11 | 10.5 | 5.1 |
| Example 23 | A3 | H18 | H24 | H4 | 14.1 | 5.2 |
| Example 24 | A5 | H23 | H22 | H15 | 12.1 | 4.8 |

The organic compound according to the present invention is a compound having a high quantum yield and light emission suitable for red emission. Therefore, when the organic compound according to the present invention is used as a constituent material of an organic electroluminescence element, an organic electroluminescence element having good emission characteristics can be produced.

Other Embodiments

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-009529, filed Jan. 20, 2011, which is hereby incorporated by reference herein in its entirety.

Reference Signs List

8: TFT element, 11: anode, 12: organic compound layer, 13: cathode

The invention claimed is:

1. An organic compound of general formula (1)

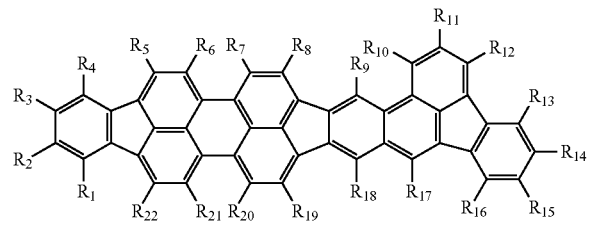

(1)

wherein in the formula (1), $R_1$ to $R_{22}$ are each independently a hydrogen atom or a substituent selected from a halogen atom, a substituted or unsubstituted alkyl group, a substituted or unsubstituted alkoxy group, a substituted or unsubstituted amino group, a substituted or unsubstituted aryl group, a substituted or unsubstituted heterocyclic group, a substituted or unsubstituted aryloxy group, a silyl group, and a cyano group.

2. The organic compound according to claim 1, wherein $R_1$ to $R_{22}$ are each independently selected from a hydrogen atom, a substituted or unsubstituted alkyl group, and a substituted or unsubstituted aryl group.

3. The organic compound according to claim 1, wherein $R_1$, $R_2$, $R_3$, $R_4$, $R_9$, and $R_{18}$ are each a hydrogen atom or a substituted or unsubstituted aryl group.

4. An organic electroluminescence element comprising:
an anode and a cathode; and
at least one organic compound layer disposed between the anode and the cathode,
wherein at least one of the at least one organic compound layer contains the organic compound according to claim 1.

5. The organic electroluminescence element according to claim 4, wherein the organic compound is contained in a light-emitting layer.

6. The organic electroluminescence element according to claim 4, wherein an emission wavelength region of the organic electroluminescence element is 580 nm or more and 650 nm or less is emitted.

7. A display device comprising:
a plurality of pixels,
wherein each of the plurality of pixels includes the organic electroluminescence element according to claim 4 and a Thin Film Transistor element electrically connected to the organic electroluminescence element.

8. An image input device comprising:
an input portion arranged to input image information; and
a display portion arranged to output an image,
wherein the display portion has a plurality of pixels, and each of the plurality of pixels includes the organic electroluminescence element according to claim 4 and a Thin Film Transistor element electrically connected to the organic electroluminescence element.

9. An illuminating device comprising the electroluminescence element according to claim 4.

10. An exposure light source of an electrophotographic image forming apparatus,
the exposure light source comprising the electroluminescence element according to claim 4.

11. An apparatus comprising the electroluminescence element according to claim 4.

12. An electrophotographic image forming apparatus comprising an exposure light source, wherein the exposure light source comprises the organic electroluminescence element according to claim 4.

\* \* \* \* \*